US010466255B2

(12) United States Patent
Allaouchiche et al.

(10) Patent No.: US 10,466,255 B2
(45) Date of Patent: Nov. 5, 2019

(54) PREDICTION OF THE RISK OF DEVELOPING A DISSEMINATED INFECTION FOR PATIENTS ADMITTED TO AN INTENSIVE CARE UNIT

(71) Applicants: BIOMÉRIEUX, Marcy l'etoile (FR); HOSPICES CIVILS DE LYON, Lyons (FR); CENTRE HOSPITALIER UNIVERSITAIRE DE NANTES, Nantes (FR)

(72) Inventors: Bernard Allaouchiche, Lyons (FR); Karim Asehnoune, Nantes (FR); Marilyne Dupin, Vaugneray (FR); Tanguy Fortin, Lyons (FR); Aurélie Gouel-Cheron, Paris (FR); Audrey Larue-Triolet, Tassin la Demi Lune (FR); Guillaume Monneret, Lyons (FR); Alexandre Pachot, Sulignat (FR); Sylvie Pons, Saint Genis les Ollieres (FR); Antoine Roquilly, Caulfield North (AU); Fabienne Venet, Lyons (FR)

(73) Assignees: BIOMERIEUX, Marcy l'Etoile (FR); HOSPICES CIVILS DE LYON, Lyons (FR); CENTRE HOSPITALIER UNIVERSITAIRE DE NANTES, Nantes (FR)

( * ) Notice: Subject to any disclaimer, the term of this patent is extended or adjusted under 35 U.S.C. 154(b) by 0 days.

(21) Appl. No.: 15/573,499

(22) PCT Filed: May 11, 2016

(86) PCT No.: PCT/FR2016/051098
§ 371 (c)(1),
(2) Date: Nov. 13, 2017

(87) PCT Pub. No.: WO2016/181066
PCT Pub. Date: Nov. 17, 2016

(65) Prior Publication Data
US 2018/0095094 A1   Apr. 5, 2018

(30) Foreign Application Priority Data

May 12, 2015   (FR) ..................................... 15 54227

(51) Int. Cl.
*G01N 31/00*   (2006.01)
*G01N 33/53*   (2006.01)
*G01N 33/68*   (2006.01)

(52) U.S. Cl.
CPC ......... *G01N 33/6893* (2013.01); *G01N 33/53* (2013.01); *G01N 2333/4703* (2013.01); *G01N 2800/26* (2013.01); *G01N 2800/50* (2013.01)

(58) Field of Classification Search
None
See application file for complete search history.

(56) References Cited

U.S. PATENT DOCUMENTS

| 8,440,622 | B2 * | 5/2013 | Stossel | ................... A61K 38/35 |
| | | | | 514/17.9 |
| 2004/0197930 | A1 | 10/2004 | Rosenfeld et al. | |
| 2007/0238668 | A1 | 10/2007 | Janmey et al. | |
| 2010/0049672 | A1 * | 2/2010 | Straube | .............. G01N 33/6887 |
| | | | | 705/500 |

FOREIGN PATENT DOCUMENTS

| FR | 2781802 A1 | 2/2000 |
| WO | 95/08000 A2 | 3/1995 |
| WO | 2013138800 A2 | 9/2013 |

OTHER PUBLICATIONS

Ali et al., "Low-Dose Recombinant Properdin Provides Substantial Protection Against *Streptococcus pneumonia* and Neisseria Meningitidis Infection". Proc Natl Acad Sci U.S.A, vol. 111, No. 14, pp. 5301-5306, 2014.
Asehnoune et al., "Hydrocortisone and Fludrocortisone for Prevention of Hospital-Acquired Pneumonia in Patients With Severe Traumatic Brain Injury (CORTIC-TC): A Double-Blind, Multicentre Phase 3, Randomized Placebo-Controlled Trial". Lancet Respir Med, vol. 2, pp. 706-176, 2014.
Bone et al., "Definitions for Sepsis and Organ Failure and Guidelines for the Use of Innovative Therapies in Sepsis". The ACCP/ SCCM Consensus Conference Committee. American College of Chest Physicians/Society of Critical Care Medicine, Chest, vol. 101, No. 6, pp. 1644-1655, 1992.
Maclean et al., "Skyline: An Open Source Document Editor for Creating and Analyzing Targeted Proteomics Experiments". Bioinformatics, vol. 26, No. 7, pp. 966-968, 2010.

(Continued)

*Primary Examiner* — Lisa V Cook
(74) *Attorney, Agent, or Firm* — Oliff PLC

(57) ABSTRACT

A method for predicting the risk of developing a disseminated infection in a patient admitted to intensive care having no clinical symptoms of such infection includes: determining a first dose of gelsolin G1 in a biological sample from the patient originating from a first sample taken at time T1, carried out between the day of intensive care admission and 48 hours afterward; determining a second dose of gelsolin G2 in a biological sample from the patient originating from a second sample taken at time T2, carried out two to three days after the first sampling; calculating the variation between the dose of gelsolin G2 and the dose of gelsolin G1, giving a Δ value; and comparing the Δ value to a threshold value S determined beforehand from two patient populations admitted to intensive care, one not having developed a disseminated infection and the other having developed such an infection.

14 Claims, 10 Drawing Sheets

Specification includes a Sequence Listing.

(56) References Cited

OTHER PUBLICATIONS

Bucki et al., "Inactivation of Endotoxin by Human Plasma Gelsolin". Biochemistry, vol. 44, pp. 9590-9597, 2005.

Chahin et al., "The Novel Immunotherapeutic Oligodeoxynucleotide IMT504 Protects Neutropenic Animals From Fatal Pseudomonas Aeruginosa Bacteremia and Sepsis". Antimicrob Agents Chemother, vol. 59, No. 2, pp. 1225-1229, 2015.

Eggimann et al., "Infection Control in the ICU". Chest, vol. 120, pp. 2059-2093, 2001.

Essader et al., "A Comparison of Immobilized pH Gradient Isoelectric Focusing and Strong-Cation-Exchange Chromatography As a First Dimension in Shotgun Proteomics". Proteomics, vol. 5, pp. 24-34, 2005.

Fortin et al., "Clinical Quantitation of Prostate-Specific Antigen Biomarker in the Low Nanogram/Milliliter Range by Conventional Bore Liquid Chromatography-Tandem Mass Spectrometry (Multiple Reaction Monitoring) Coupling and Correlation With Elisa Tests". Mol. Cell Proteomics, vol. 8, No. 5, pp. 1006-1015, 2009.

Hanley et al., "The Meaning and Use of the Area Under a Receiver Operating Characteristic (ROC) Curve". vol. 143, pp. 29-36, 1982.

Jensen et al., "Procalcitonin-Guided Interventions Against Infections to Increase Early Appropriate Antibiotics and Improve Survival in the Intensive Care Unti: A Randomized Trail". Crit Care Med, vol. 39, No. 9, pp. 2048-2058, 2011.

Lambert et al., "Clinical Outcomes of Health-Care-Associated Infections and Antimicrobial Resistance in Patients Admitted to European Intensive-Care Untis: A Cohort Study". Lancet Infect Dis, vol. 11, pp. 30-38, 2011.

Lee et al., "Plasma Glesolin Depletion and Circulating Actin in Sepsis: A Pilot Study". PLoS One, vol. 3, No. 11, e3712, pp. 1-5, 2008.

Li et al., "Multifunctional Roles of Gelsolin in Health and Disease". Med Res Rev, vol. 32, No. 5, pp. 999-1025, 2012.

Michel et al., "Protein Fractionation in a Multicompartment Device Using Off-Gel Isoelectric Focusing". Electrophoresis, vol. 24, pp. 3-11, 2003.

Oschsner et al , "Systematic Selection of Modified Aptamer Paris for Diagnostic Sandwich Assays", BioTechniques, vol. 56, pp. 125-133, 2014.

Puisieux et al., "Prophylactic Antibiotherapy Using Cefapirin in the Surgery of Duodenal Ulcer: A Randomized Clinical Trial". Ann Fr Anesth Reanim, vol. 12, No. 3, pp. 289-292, 1993.

Vincent, JL., "Nosocomial Infections in Adult Intensive-Care Units". Lancet, vol. 361(9374), pp. 2068-2077, 2003.

Wang et al., "Time Course of Plasma Gelsolin Concentrations During Severe Sepsis in Critically Ill Surgical Patients". Crit Care, vol. 12, No. 4, pp. R106, 2008.

Xianhui et al., "The Association Between Plasma Gelsolin Level and Prognosis of Burn Patients". Bums, vol. 40, No. 8, pp. 1552-1555, 2014.

Zweig et al., "Receiver-Operating Characteristic (ROC) Plots: A Fundamental Evaluation Tool in Clinical Medicine". Clin. Chem., vol. 39, No. 4, pp. 561-577, 1993.

Aug. 8, 2016 Written Opinion issued in International Patent Application No. PCT/FR2016/051098.

Aug. 8, 2016 International Search Report issued in International Patent Application No. PCT/FR2016/051098.

Bucki et al., "Plasma Gelsolin: Function, Prognostic Value, and Potential Therapeutic Use". Current Protein and Peptide Science, vol. 9, pp. 541-551, 2008.

Mounzer et al., "Relationship of Admission Plasma Gelsolin Levels to Clinical Outcomes in Patients After Major Trauma". American Journal of Respiratory and Critical Care Medicine, vol. 160, pp. 1673-1681, 1999.

Huang et al., "Reduction of Plasma Gelsolin Levels Correlates With Development of Multiple Organ Dysfunction Snydrome and Fatal Outcome in Burn Patients". pLos One, vol. 6, No. 11, e25748, pp. 1-9, 2011.

\* cited by examiner

SEQUENCE LISTING

```
<160> NUMBER OF SEQ ID NOS: 4

<210> SEQ ID NO 1
<211> LENGTH: 782
<212> TYPE: PRT
<213> ORGANISM: Homo sapiens

<400> SEQUENCE: 1

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

Pro Asn Ser Met Val Val Glu His Pro Glu Phe Leu Lys Ala Gly Lys
    50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
                85                  90                  95

Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
        115                 120                 125

Ala Ile Phe Thr Val Gln Leu Asp Asp Tyr Leu Asn Gly Arg Ala Val
    130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Gly Val Ala Ser Gly Phe
                165                 170                 175

Lys His Val Val Pro Asn Glu Val Val Val Gln Arg Leu Phe Gln Val
            180                 185                 190

Lys Gly Arg Arg Val Val Arg Ala Thr Glu Val Pro Val Ser Trp Glu
        195                 200                 205

Ser Phe Asn Asn Gly Asp Cys Phe Ile Leu Asp Leu Gly Asn Asn Ile
    210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
            260                 265                 270
```

-continued

```
Val Leu Gly Pro Lys Pro Ala Leu Pro Ala Gly Thr Glu Asp Thr Ala
            275                 280                 285
Lys Glu Asp Ala Ala Asn Arg Lys Leu Ala Lys Leu Tyr Lys Val Ser
290                 295                 300
Asn Gly Ala Gly Thr Met Ser Val Ser Leu Val Ala Asp Glu Asn Pro
305                 310                 315                 320
Phe Ala Gln Gly Ala Leu Lys Ser Glu Asp Cys Phe Ile Leu Asp His
                325                 330                 335
Gly Lys Asp Gly Lys Ile Phe Val Trp Lys Gly Lys Gln Ala Asn Thr
            340                 345                 350
Glu Glu Arg Lys Ala Ala Leu Lys Thr Ala Ser Asp Phe Ile Thr Lys
        355                 360                 365
Met Asp Tyr Pro Lys Gln Thr Gln Val Ser Val Leu Pro Glu Gly Gly
370                 375                 380
Glu Thr Pro Leu Phe Lys Gln Phe Phe Lys Asn Trp Arg Asp Pro Asp
385                 390                 395                 400
Gln Thr Asp Gly Leu Gly Leu Ser Tyr Leu Ser Ser His Ile Ala Asn
                405                 410                 415
Val Glu Arg Val Pro Phe Asp Ala Ala Thr Leu His Thr Ser Thr Ala
            420                 425                 430
Met Ala Ala Gln His Gly Met Asp Asp Gly Thr Gly Gln Lys Gln
        435                 440                 445
Ile Trp Arg Ile Glu Gly Ser Asn Lys Val Pro Val Asp Pro Ala Thr
450                 455                 460
Tyr Gly Gln Phe Tyr Gly Gly Asp Ser Tyr Ile Ile Leu Tyr Asn Tyr
465                 470                 475                 480
Arg His Gly Gly Arg Gln Gly Gln Ile Ile Tyr Asn Trp Gln Gly Ala
                485                 490                 495
Gln Ser Thr Gln Asp Glu Val Ala Ala Ser Ala Ile Leu Thr Ala Gln
            500                 505                 510
Leu Asp Glu Glu Leu Gly Gly Thr Pro Val Gln Ser Arg Val Val Gln
        515                 520                 525
Gly Lys Glu Pro Ala His Leu Met Ser Leu Phe Gly Gly Lys Pro Met
530                 535                 540
Ile Ile Tyr Lys Gly Gly Thr Ser Arg Glu Gly Gly Gln Thr Ala Pro
545                 550                 555                 560
Ala Ser Thr Arg Leu Phe Gln Val Arg Ala Asn Ser Ala Gly Ala Thr
                565                 570                 575
Arg Ala Val Glu Val Leu Pro Lys Ala Gly Ala Leu Asn Ser Asn Asp
            580                 585                 590
Ala Phe Val Leu Lys Thr Pro Ser Ala Ala Tyr Leu Trp Val Gly Thr
        595                 600                 605
Gly Ala Ser Glu Ala Glu Lys Thr Gly Ala Gln Glu Leu Leu Arg Val
610                 615                 620
Leu Arg Ala Gln Pro Val Gln Val Ala Glu Gly Ser Glu Pro Asp Gly
625                 630                 635                 640
Phe Trp Glu Ala Leu Gly Gly Lys Ala Ala Tyr Arg Thr Ser Pro Arg
                645                 650                 655
Leu Lys Asp Lys Lys Met Asp Ala His Pro Pro Arg Leu Phe Ala Cys
            660                 665                 670
Ser Asn Lys Ile Gly Arg Phe Val Ile Glu Glu Val Pro Gly Glu Leu
        675                 680                 685
Met Gln Glu Asp Leu Ala Thr Asp Asp Val Met Leu Leu Asp Thr Trp
```

```
                    690                 695                 700

Asp Gln Val Phe Val Trp Val Gly Lys Asp Ser Gln Glu Glu Lys
705                     710                 715                 720

Thr Glu Ala Leu Thr Ser Ala Lys Arg Tyr Ile Glu Thr Asp Pro Ala
                    725                 730                 735

Asn Arg Asp Arg Arg Thr Pro Ile Thr Val Val Lys Gln Gly Phe Glu
                740                 745                 750

Pro Pro Ser Phe Val Gly Trp Phe Leu Gly Trp Asp Asp Asp Tyr Trp
            755                 760                 765

Ser Val Asp Pro Leu Asp Arg Ala Met Ala Glu Leu Ala Ala
        770                 775                 780

<210> SEQ ID NO 2
<211> LENGTH: 11
<212> TYPE: PRT
<213> ORGANISM: Artificial Sequence
<220> FEATURE:
<223> OTHER INFORMATION: Peptide

<400> SEQUENCE: 2

His Val Val Pro Asn Glu Val Val Val Gln Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Peptide

<400> SEQUENCE: 3

Ala Gly Ala Leu Asn Ser Asn Asp Ala Phe Val Leu Lys
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Peptide

<400> SEQUENCE: 4

Gln Thr Gln Val Ser Val Leu Pro Glu Gly Gly Glu Thr Pro Leu Phe
1               5                   10                  15

Lys
```

PREDICTION OF THE RISK OF DEVELOPING A DISSEMINATED INFECTION FOR PATIENTS ADMITTED TO AN INTENSIVE CARE UNIT

The present invention relates to the field of infectious diseases. More particularly, the present invention relates to a method for predicting the risk, for patients admitted to intensive care, of developing a disseminated infection, or septic syndrome, by the use of gelsolin as a biomarker.

Septic syndrome, a systemic response to an infection, also referred to as disseminated infection, is one of the leading causes of death in intensive care. Indeed, patients treated in intensive care are vulnerable patients who have, or are likely to have, one or more acute visceral malfunctions that directly affect their prognosis of survival. The causes which may lead to a patient being admitted to intensive care are numerous: states of shock, multiple trauma, comas, acute organic insufficiencies, decompensations from chronic diseases, hemorrhages, poisonings, severe infections, extensive burns, postoperative period following heavy surgeries, etc. In general, patients requiring intensive care are suffering from organ failure such as hemodynamic instability (hypotension/hypertension), respiratory distress, acute renal insufficiency, severe cardiac arrhythmia, neurological disorders (cranial trauma, stroke, coma), etc. The frequent combination thereof is referred to as multi-visceral failure. Indeed, one of these failures often leads to another, since most organ systems are linked to one another.

A stay in intensive care involves continuous monitoring of vital functions and, where appropriate, the use of supplementation methods (transfusion of blood derivatives, vascular filling, mechanical ventilation, catecholamines, hemodialysis, extracorporeal circulation, etc.). The ultimate goal of intensive care is the restoration of homeostasis.

As a result, patients admitted to intensive care are at risk of contracting a nosocomial infection, of bacterial, viral, fungal or parasitic origin.

A nosocomial infection is defined as an infection contracted in the hospital, that is to say which is not present when the patient is admitted to hospital, in this case to intensive care, and which breaks out at least 48 hours after admission. Nosocomial infection can affect any part of the body, but the most common in intensive care are pneumonias associated with mechanical ventilation, intra-abdominal infections following trauma or surgery, urinary tract infections (or UTIs) and bacteremia related to intravascular devices (Vincent J L, Lancet, 2003; Eggiman P, Chest, 2001).

The prevalence of nosocomial infections is significantly higher in intensive care than that observed in other hospital sectors, resulting from the deleterious convergence of several endogenous risk factors: exposing the patient to invasive procedures (artificial ventilation, urinary catheterization, catheterization), patient severity (as well as associated comorbidities) and therapies (multiple transfusions, sedation). Nevertheless, despite all the hygiene and monitoring measures (exogenous risks) put in place and taking into account these endogenous risk factors, the incidence of nosocomial infections has remained stable or decreased slightly over the years.

A nosocomial infection is liable to cause a disseminated infection, or septic syndrome, which can evolve from simple sepsis to severe sepsis or even to septic shock.

These three clinical syndromes, sepsis, severe sepsis and septic shock were defined in increasing order of severity in 1992 by a panel of experts (R. C. Bone et al., 1992):

Sepsis is thus a systemic inflammatory response linked to an infection,

Severe sepsis is sepsis accompanied by the dysfunction of at least one organ,

Septic shock is severe sepsis combined with persistent hypotension and may be qualified by:
  The presence of an identified infectious site,
  A generalized inflammatory response manifested by at least three of the following signs: a) temperature above 38° C. or below 36° C., b) heart rate greater than 90 beats per minute, c) respiratory rate greater than 20 breaths per minute, d) number of leukocytes greater than 12 000/mm$^3$ or less than 4000/mm$^3$,
  Persistent hypotension despite adequate filling and vasopressor treatments.

Identifying those patients most at risk of contracting a disseminated infection as soon as they are admitted and in the absence of any symptoms of disseminated infection would make it possible to implement a strategy as soon as possible in order to limit their risk of developing such an infection. For example, a prophylactic antibiotic treatment could be administered (Puisieux F et al., 1993; Jensen J U et al., 2011) or else a preventative treatment (K. Asehnoune et al., 2014) or else targeted immunotherapy (Chahin A et al., 2015; Ali Y M et al., 2014), or, more simply, points of entry for pathogens could be limited (i.e. withdrawal of catheters as soon as possible, etc.). These measures would allow better treatment of the patient, leading to:
  a reduction in the length of hospitalization in intensive care and in the hospital, which makes it possible to reduce associated costs (Lambert M L S C et al., 2011);
  a reduction in septic complications; and
  a reduction in the mortality rate.

There is therefore an urgent need, which has not been met for many years, to find the right tools to be able to predict, in patients admitted to intensive care and who have no clinical symptoms of disseminated infection, who are the most at risk of developing a disseminated infection and thus allowing their stratification as soon as they are admitted, as a function of their risk of developing this type of infection.

Surprisingly, the Applicants have demonstrated that such a prediction was made possible by analyzing the dose of gelsolin in a biological sample originating from the patient admitted to intensive care. Indeed, the Applicants have shown that patients at high risk of developing such a disseminated infection had a greatly reduced level of gelsolin. The invention thus presents an important step forward in the field of combating the development of disseminated infections, which is one of the leading causes of mortality in at-risk patients within the context of admission to intensive care, which patients do not exhibit symptoms of disseminated infection when they are admitted.

Thus, the first subject of the present invention is a method for predicting the risk of developing a disseminated infection in a patient admitted to intensive care having no clinical symptoms of such an infection, comprising or consisting of the following steps:
  determining a first dose of gelsolin G1 in a biological sample from said patient originating from a first sample taken at the time T1, carried out between the day of admission to intensive care and 48 hours afterward,
  determining a second dose of gelsolin G2 in a biological sample from said patient originating from a second sample taken at the time T2, carried out two to three days after the first sampling,
  calculating the variation between the dose of gelsolin G2 and the dose of gelsolin G1, giving a Δ value, comparing the Δ value obtained in the preceding step to a threshold value S determined beforehand from two populations of patients admitted to intensive care, one not having developed a disseminated infection and the other having developed such an infection, a Δ value lower than said threshold value S meaning that the patient admitted to intensive care is a patient at high risk of developing a disseminated infection, and a Δ value greater than said threshold value S meaning that the patient admitted to intensive care is not a patient at high risk of developing a disseminated infection.

The Applicants have therefore unexpectedly shown that it is possible to predict the risk of developing a disseminated infection in a patient admitted to intensive care using gelsolin as a marker.

According to the present invention, patients admitted to intensive care are patients who have, or are likely to have, several acute, directly life-threatening visceral malfunctions which involve the use of supplementation methods. These patients are, for example, multiple-trauma patients, what are referred to as major burns patients, patients suffering from pancreatitis or else acute respiratory syndrome. These patients are therefore particularly vulnerable to nosocomial infections that may progress to a disseminated infection.

According to the present invention, a disseminated infection is a non-localized infection, widespread within the body and caused by pathogens such as bacteria, fungi, viruses or parasites. Reference is also made to septic syndrome.

Predicting the risk of developing a disseminated infection is intended to mean the identification of patients without symptoms of disseminated infection at the time of admission to intensive care, that is to say without any clinical manifestations of such a disseminated infection, who will develop it in the days following their admission to intensive care, on average 5 days after they have been admitted. In other words, predicting the risk of developing a disseminated infection is intended to mean determining such a risk in a patient admitted to intensive care who has no symptoms of disseminated infection at the time of admission to intensive care. Patients most at risk of developing a disseminated infection, for whom a strategy to limit their risk of developing such an infection should be put in place as soon as possible, are referred to as high-risk patients. For these high-risk patients, the use of gelsolin makes it possible to predict the occurrence of a disseminated infection. In other words, a high-risk patient is a patient whose probability of developing a disseminated infection is at least 75%.

Within the context of the present invention, the infection is said to be early, that is to say, it will occur in the 5 days following admission of the patients into intensive care.

The marker used in the present invention for predicting the risk of developing a disseminated infection is gelsolin. It is a protein having a molecular weight of between 82 and 84 kDa (Swiss Prot No. P06396), being cytosolic and comprising 6 domains (G1 to G6) capable of binding to actin monomers or actin filaments in the presence of a high concentration of calcium ions. This binding can be regulated by pH, phosphoinositides, lysophosphatidic acid and high calcium concentrations. The actin monomer binding sites are present in the G1 domain and also in the G4-6 segment, while the high-affinity site for binding to actin filaments is in the G2-3 segment. Gelsolin then plays a repair role in tissue damage. There are 4 known isoforms of the protein, the main one of which being isoform 1 (Swiss Prot No. P06396-1) which is the secreted plasma form of the protein. The cytoplasmic isoform 2 (Swiss Prot No. P06396-2) differs from the isoform 1 by the deletion of the first 51 amino acids. The cytoplasmic isoforms 3 and 4 (Swiss Prot Nos. P06396-3 and P06396-4) differ from the isoform 1 by a modification of the sequence of the first 48 amino acids.

Within the context of the present invention, all the isoforms of gelsolin can be used as a marker to predict the risk of developing a disseminated infection in a patient admitted to intensive care. According to one embodiment, the isoform assayed is isoform 1.

Gelsolin is known to be involved in many pathologies, especially in different types of cancers, in certain inflammatory and infectious contexts, in the case of cardiac and pulmonary diseases, in Alzheimer's disease or else aging.

This protein has already been described as a marker in the scientific literature:

either for the diagnosis of a septic syndrome, that is to say identifying patients already suffering from a septic syndrome and having clinical symptoms of infection (Lee et al., 2008), by making a link with the severity and prediction of mortality (Xianhui et al., 2014), or for the prognosis of the evolution of the septic syndrome in septic patients, that is to say estimating this negative evolution in patients already identified as having a disseminated infection (Wang et al., 2008), or for the prediction of mortality in septic patients, that is to say estimating the risk of mortality in patients already identified as having a disseminated infection (Wang et al., 2008).

However, in no case has gelsolin been described for the prediction of the risk of developing a disseminated infection in vulnerable, at-risk patients, such as patients admitted to intensive care, for whom no clinical manifestation of disseminated infection is present.

The prediction of the risk of developing a disseminated infection in patients admitted to intensive care is implemented by the determination of a dose of gelsolin in a biological sample from said patient.

Generally, the term "sample" refers to a portion or to an amount, more particularly a small portion or a small amount, taken from one or more entities for the purposes of analysis. This sample may optionally have undergone a prior treatment, involving, for example, mixing and diluting steps.

Within the context of the method of the invention, the sample is a biological sample originating from the patient in whom it is desired to determine the risk of developing a disseminated infection. In particular, such a biological sample is chosen from those liable to contain gelsolin.

The biological sample according to the present invention may be of different natures. In particular, this sample is a biological fluid, for example chosen from blood, whole blood (as collected via the venous route, i.e. containing white and red blood cells, platelets and plasma), serum, plasma, bronchoalveolar lavage fluid, cerebrospinal fluid, and urine. Preferably, the biological sample originating from the patient is a sample of whole blood, plasma, serum or any derivative.

"Dose of gelsolin" is intended to mean an amount of gelsolin in said biological sample. Sometimes it is not the dose that is given as the final result of the method, but the concentration of gelsolin, which is calculated from the dose by dividing the dose by the volume of the sample on which the measurement is made. For the purposes of the invention, the dose or the concentration of gelsolin will both be referred to as "dose".

The dose of gelsolin in a biological sample may be determined according to techniques widely known to those skilled in the art for determining the amount, or dose, of an analyte in a biological sample. By way of examples, mention may be made of immunoassays such as ELISA (Enzyme Linked ImmunoSorbent Assay), ELFA (Enzyme Linked Fluorescent Assay) and RIA (Radio ImmunoAssay), and mass spectrometry assays, which constitutes an embodiment of the invention.

Immunoassay is a method well known to those skilled in the art which is widely used in the field of biological sample analysis. It makes it possible to detect analytes in samples, especially in the form of proteins (antigens/antibodies), peptides and haptens, such as, for example, steroids or vitamins, involving immunological reactions between the analyte to be detected, in the present case gelsolin, and one or more binding partner(s) to this analyte. These immunoassay methods are based on measurements making it possible to quantify the signals emitted during the analysis of the biological sample. The amount of signals detected is generally proportional to the amount, or dose, of analyte to measure (for example during a sandwich assay) or inversely proportional to the amount, or dose, of analyte to measure (for example competitive assay). Of course, the term "immuno", in "immunoassay" for example, is not to be considered in the present application to strictly indicate that the binding partner is an immunological partner such as an antibody. Indeed, those skilled in the art also widely use this term when the binding partner, also referred to as ligand, is not an immunological partner but is, for example, a receptor for the analyte that it is desired to assay. Thus, it is known to refer to the ELISA assay ("Enzyme-Linked ImmunoSorbent Assay") for assays which use non-immunological binding partners, more commonly referred to as "Ligand Binding Assay", even though the term "immuno" is included in the acronym ELISA. For the purposes of clarity, the Applicants will use the term "immuno" throughout the application for any assay using a binding partner, even when it is not an immunological partner.

As a binding partner to gelsolin, mention may be made of antibodies, antibody fractions, nanofitins, aptamers (Ochsner U. A. et al., 2014) or any other molecule which is known to have an interaction with the gelsolin being studied, such as lipopolysaccharides (Bucki R. et al., 2005).

The binding partner antibodies are, for example, either polyclonal antibodies or monoclonal antibodies, the production of which is widely known to those skilled in the art. Such antibodies are commercially available, such as, for example, the following polyclonal antibodies: Anti-Gelsolin plasma Goat polyclonal antibody, ABCAM, anti-Gelsolin polyclonal antibody SHEEP 1, Thermo Pierce ANBOP0000269032, and the following monoclonal antibodies: Monoclonal anti-gelsolin 1, Boster Biological Technology ANBOP0000215379.

By way of example of antibody fragments, mention may be made of the Fab, Fab', F(ab')2 fragments, and also the scFv (Single chain variable fragment) and dsFv (Double-stranded variable fragment) chains. These functional fragments may especially be obtained by genetic engineering.

The immunoassay consisting in determining the dose of gelsolin is a quantitative assay which is widely known to those skilled in the art, preferably employing two binding partners to gelsolin. One of the two partners may be coupled to a label to form a conjugate or tracer. The other binding partner may be captured on a solid support. Reference is then made to capture partner for the latter and detection partner for the former.

As indicated above, the measured signal emitted during the immunoassay is then proportional to the amount, or dose, of gelsolin in the biological sample.

To correlate the signal obtained to the dose, or to the concentration in the biological sample, it is suitable to use a mathematical model pre-established from a standard range. This standard range will be obtained beforehand in a known manner. Briefly, obtaining a standard range consists in measuring the signal generated by increasing and known amounts or concentrations of gelsolin, in plotting the curve which gives the signal as a function of the dose, or concentration, and in finding a mathematical model that represents this relationship as closely as possible. The mathematical model will be used to determine, by extrapolation, the unknown doses, or concentrations, of gelsolin contained in the biological sample to be tested.

Label used to form the conjugate is intended to mean, especially, any molecule containing a group which reacts with a group of the binding partner, directly without chemical modification or after chemical modification to include such a group, which molecule is capable of directly or indirectly generating a detectable signal. A non-limiting list of these direct detection labels consists of:
  enzymes which produce a detectable signal, for example by colorimetry, fluorescence, luminescence, such as horseradish peroxidase, alkaline phosphatase, β-galactosidase, glucose-6-phosphate dehydrogenase,
  chromophores such as fluorescent, luminescent or coloring compounds,
  radioactive molecules such as $^{32}P$, $^{35}S$ or $^{125}I$,
  fluorescent molecules such as Alexa or phycocyanins, and
  electrochemiluminescent salts, such as organometallic derivatives based on acridinium or ruthenium.

Indirect detection systems can also be used, such as, for example, ligands capable of reacting with an anti-ligand. The ligand then corresponds to the label so as to form, with the binding partner, the conjugate.

The ligand/anti-ligand pairs are well known to those skilled in the art, which is the case, for example, of the following pairs: biotin/streptavidin, hapten/antibody, antigen/antibody, peptide/antibody, sugar/lectin, polynucleotide/sequence complementary to the polynucleotide.

The anti-ligand can then be directly detectable via the direct detection labels described above or can itself be detectable via another ligand/anti-ligand pair, and so on.

These indirect detection systems can, under certain conditions, result in an amplification of the signal. This signal amplification technique is well known to those skilled in the art, and reference may be made to the prior patent applications FR 2781802 or WO 95/08000 from one of the Applicants.

Depending on the type of labeling used, those skilled in the art will add reagents enabling the visualization of the label or the emission of a signal that is detectable by any type of appropriate measuring apparatus, such as, for example, a spectrophotometer, a spectrofluorometer, a densitometer or else a high-definition camera.

The immunoassay may also include other steps known to those skilled in the art, such as washing steps and incubation steps.

The immunoassay may be a one-step or a two-step assay, as is widely known to those skilled in the art. Briefly, a one-step immunoassay comprises bringing the sample to be tested into contact with the two binding partners simultaneously, whereas a two-step immunoassay comprises on the one hand bringing the sample to be tested into contact with the first binding partner, then the analyte-first binding partner complex thus formed is brought into contact with the second binding partner.

Mass spectrometry, which can replace the techniques developed previously, such as, especially, ELISA assays, is a method widely known to those skilled in the art. It is carried out in a mass spectrometer. It is a powerful tool increasingly used for the analysis and detection of different types of molecules in biological samples. In general, any type of molecule that can be ionized can be detected according to its molecular mass using a mass spectrometer. Depending on the nature of the molecule to be detected, of protein or metabolic origin, some mass spectrometry technologies may be more suitable. Nevertheless, regardless of the method of mass spectrometry used for detection, the latter comprises a step of ionizing the target molecule into what are referred to as molecular ions and a step of separating the molecular ions obtained as a function of their mass. A mass spectrometer measures the ratio of the mass to the charge (m/z) of ionized molecules which is correlated to the target molecule to be analyzed.

All mass spectrometers therefore comprise:
i) an ionization source intended to ionize the markers present in the sample to be analyzed, that is to say to impart a positive or negative charge to these markers;
ii) a mass analyzer intended to separate the ionized markers, or molecular ions, as a function of their mass-to-charge ratio (m/z);
iii) a detector intended to measure the signal produced either directly by the molecular ions or by ions produced from the molecular ions, as detailed below.

The ionization step required for carrying out mass spectrometry can be carried out by any method known to those skilled in the art. The ionization source makes it possible to place the molecules to be assayed in a gaseous and ionized state. An ionization source can be used either in positive mode to study positive ions or in negative mode to study negative ions. Several types of sources exist and will be used as a function of the desired result and the molecules analyzed. Mention may be made, especially, of:
electron ionization (EI), chemical ionization (CI) and desorption chemical ionization (DCI),
bombardment by fast atoms (FAB), metastable atoms (MAB) or ions (SIMS, LSIMS),
inductively coupled plasma (ICP),
atmospheric-pressure chemical ionization (APCI) and atmospheric pressure photoionization (APPI),
electrospray (ESI),
matrix-assisted laser desorption/ionization (MALDI), surface-enhanced laser desorption/ionization (SELDI) or desorption/ionization on silicon (DIOS), and
ionization/desorption by interaction with metastable species (DART).

The mass analyzer, in which the step of separating the ionized markers as a function of their mass/charge ratio (m/z) is carried out, is any mass analyzer known to those skilled in the art. Mention may be made of low-resolution analyzers of quadrupole (Q) type, 3D (IT) or linear (LIT) ion trap type, and high-resolution analyzers, making it possible to measure the exact mass of the analytes and using especially the magnetic sector coupled to an electrical sector, time of flight (TOF).

Separation of the molecular ions according to their m/z ratio can be carried out once (single mass spectrometry or MS), or else several successive MS separations can be performed. When two successive MS separations are carried out, the analysis is called MS/MS or $MS^2$. When three successive MS separations are carried out, the analysis is called MS/MS/MS or $MS^3$ and, more generally, when n successive MS separations are carried out, the analysis is called $MS^n$.

The SRM (Selected Reaction Monitoring) mode of analysis using two successive separations of single mass spectrometry is a particular use of $MS^2$ separation.

This SRM detection in MS/MS mode comprises two additional steps relative to the MS mode, which are a fragmentation of the molecular ions, then referred to as precursor ions, to give fragment ions (or daughter ions), and a separation of the fragment ions as a function of their mass. It is then the m/z ratio of the fragment ions which is correlated with the target molecule to be analyzed. The principle of the SRM mode is to specifically select a precursor ion, to fragment it, and then to specifically select one of its fragment ions. For such applications, devices of the "triple quadrupole" type or "triple quadrupole with ion trap" hybrids are generally used.

In the case of a "triple quadrupole" or "quadrupole with ion trap" device (Q1q2Q3) used in $MS^2$ mode, with a view to assaying or detecting a target protein, the first quadrupole (Q1) makes it possible to filter the molecular ions, corresponding to the proteotypic peptides characteristic of the protein to be assayed and obtained during a prior digestion step, which will be detailed below, as a function of their mass to charge (m/z) ratio. Only the peptides having the mass/charge ratio of the proteotypic peptide sought, said ratio being referred to as $(m/z)_1$, are transmitted to the second quadrupole (q2) and act as precursor ions for the subsequent fragmentation. The q2 analyzer makes it possible to fragment the peptides of mass/charge ratio $(m/z)_1$ into first-generation fragment ions. The fragmentation is generally obtained by collision of the precursor peptides with an inert gas, such as nitrogen or argon in q2. The first-generation fragment ions are transmitted to a third quadrupole (Q3) which filters the first-generation fragment ions as a function of a specific mass-to-charge ratio, said ratio being referred to as $(m/z)_2$. Only the first-generation fragment ions having the mass/charge ratio of a fragment characteristic of the proteotypic peptide sought $(m/z)_2$ are transmitted to the detector in order to detected, or even quantified.

This operating mode has a double selectivity, in relation, on the one hand, to the selection of the precursor ion and, on the other hand, to the selection of the first-generation fragment ion. Mass spectrometry in SRM mode is thus advantageous for quantification.

Within the context of the invention, the mass spectrometer of "triple quadrupole" or "quadrupole ion trap" type may be coupled to a chromatography chosen from affinity chromatography and high performance liquid chromatography (HPLC). Preferably, the mass spectrometer is coupled to a high performance liquid chromatography system (HPLC).

As mentioned above, upstream of the detection by mass spectrometry, the sample to be analyzed is preferentially pretreated to generate peptides from the proteins present in the sample, for example by digestion with a proteolytic (protease) enzyme, or by the action of a chemical reagent. Indeed, the cleavage of the proteins can be done by a physicochemical treatment, by a biological treatment or by a combination of the two treatments. The treatment of the proteins by enzymatic digestion is nevertheless preferred over physicochemical treatment because it further preserves the structure of the proteins and is easier to control.

"Enzymatic digestion" is intended to mean the single or combined action of one or more enzymes under appropriate reaction conditions. Enzymes which perform proteolysis, referred to as proteases, cut proteins at specific locations. Within the context of the invention, the sample is preferably digested by the action of a protease enzyme, for example trypsin which cleaves the peptide bond at the carboxylic group of arginine (R) and lysine (K) residues.

Among the peptides thus obtained, the peptides characteristic of the protein to be assayed are referred to as proteotypic peptides. These are the peptides that will be subsequently monitored and quantified by mass spectrometry. The quantitative determination of proteins by mass spectrometry techniques via their proteotypic peptides has already been validated in complex fluids (Fortin T. et al., 2009).

The proteotypic peptides of interest are chosen according to their specificity in the matrix (by virtue of the Peptide Atlas software freely available on the internet) and their sensitivity (better response in the mass spectrometer).

Depending on the complexity of the sample, the digestion step may be followed by a step of fractionation of the peptides present in the sample of interest, to reduce its complexity. Fractionation is intended to mean, in a conventional manner, a purification of the number of peptides present. Such fractionation may be carried out by a technique known to those skilled in the art, such as, for example, solid phase extraction (SPE), "off gel" fractionation (Michel P E. et al., 2003) or the technique of immobilized pH gradient isoelectric focusing (Essader A S et al., 2005).

One of the advantages of using mass spectrometry is that it is particularly useful for quantifying molecules, in this case a protein marker such as gelsolin. For this purpose, the detected current intensity is used, which is proportional to the amount of target molecule. The current intensity thus measured can be used as a quantitative measure to be able to determine the amount of target molecule present. This is because the current intensity induced by the selected daughter ion(s), measured in the detector, is proportional to the amount of parent ions, which is itself proportional to the amount of proteotypic peptides, which is itself proportional to the amount of the molecule of interest to be assayed. The amount of current measured, induced by the daughter ions, is therefore directly proportional to the amount of the molecule to be assayed. The selection of at least one quantitative measurement associated with at least one daughter ion and the correlation of this quantitative measurement with the amount of molecule present in the sample makes it possible to obtain a quantitative assay.

As with immunoassay, calibration is nevertheless necessary. This makes it possible to correlate the measured area of the peak, corresponding to the current intensity induced by the detected ions, to the amount of target molecule to be assayed. For this purpose, the calibrations conventionally used in mass spectrometry may be employed, within the scope of the invention. SRM assays are conventionally calibrated using external standards or, preferably, using internal standards as described by T. Fortin et al., 2009. In the case in which the target molecule is a proteotypic peptide, which makes it possible to assay a protein of interest, the correlation between the quantitative measurement and the amount of target proteotypic peptide, and consequently of protein of interest, is obtained by calibrating the signal measured relative to a standard signal for which the amount to be assayed is known. The calibration may be carried out by means of a calibration curve, for example obtained by successive injections of standard proteotypic peptide at different concentrations (external calibration), or preferentially by internal calibration using a heavy peptide as internal standard in accordance with the AQUA ("absolute quantification") method. "Heavy peptides" is intended to mean synthetic peptides, the amino acid sequences of which are identical to the selected target proteotypic peptides (molecular ions) but for which some of the carbon 12 atoms ($^{12}C$) are replaced by carbon 13 ($^{13}C$) and/or the nitrogen 14 atoms ($^{14}N$) are replaced by nitrogen 15 ($^{15}N$). Indeed, these heavy peptides have the same physicochemical properties as the target natural peptides (with the exception of a higher mass) and are eluted at the same chromatographic retention times. These peptides constitute the internal standard (IS). They will be added in fixed amounts to each sample upstream of the mass spectrometry assay, for example upstream of the protein digestion in the sample of interest. Thus, the synthetic peptides undergo the same treatment steps as the target proteins and are co-purified with the natural target peptides to be assayed during the peptide fractionation. They are injected simultaneously into the mass spectrometer for the assay. The comparison of the areas of the peak of the natural peptides to be assayed (analytes) with the areas of the peaks of the heavy peptides (internal standard) makes it possible to carry out a relative quantification of the protein of the target natural peptide and thereby to work back to the relative amount of the protein to be assayed.

The dose of gelsolin in a biological sample may be determined at least twice, at two different times T1 and T2. The biological samples taken at T1 and T2 are of the same nature. Preferably, the biological samples taken at T1 and T2 are blood samples such as whole blood, plasma, serum or any blood derivative.

The first determination of the dose of gelsolin, which dose is referred to as G1, is carried out at a time T1 in a biological sample taken between the day of admission to intensive care and 48 hours afterward. According to one embodiment, the first determination of the dose of gelsolin (G1) is carried out within the first 48 hours following admission. According to another embodiment, the first determination of the dose of gelsolin (G1) is carried out on the day of admission to intensive care.

The second determination of the dose of gelsolin, which dose is referred to as G2, is carried out at a time T2 in a biological sample taken two to three days after the first sampling, i.e. three to five days after the day of admission. According to one embodiment, the second determination of the dose of gelsolin (G2) is carried out between 72 and 120 hours following admission.

According to the present invention, the method used to determine the first dose of gelsolin G1 and the second dose of gelsolin G2 is the same and is as described previously.

After determining the second dose G2, the method for predicting the risk of developing a disseminated infection according to the invention comprises a step of calculating the variation between the dose of gelsolin G2 and the dose of gelsolin G1, giving a Δ value.

The Δ value can be calculated by any calculation known to those skilled in the art making it possible to demonstrate a difference between G2 and G1.

According to one particular embodiment, the Δ value is calculated according to the following formula (I):

$$G2 - G1 \qquad (I).$$

In this case, the Δ value is of the same magnitude as the determined dose G2 or G1.

According to another particular embodiment, the Δ value corresponds to the relative rate of change and is calculated according to the following formula (II):

$$\frac{G2 - G1}{G1} \times 100 \quad \text{(II)}$$

In this case, the Δ value is a percentage.

According to another particular embodiment, the Δ value corresponds to the difference in dose per unit time and is calculated according to the following formula (III):

$$\frac{G2 - G1}{T2 - T1} \quad \text{(III)}$$

In this case, the Δ value has a unit of dose per unit of time as its magnitude.

The method for predicting the risk of developing a disseminated infection in a patient admitted to intensive care comprises a step of comparing the Δ value obtained in the preceding step to a reference value S determined beforehand from two populations of patients admitted to intensive care, one not having developed a disseminated infection and the other having developed such an infection.

This value S is always a negative value because the Applicants have unexpectedly shown that the dose of gelsolin decreased greatly between T2 and T1 for patients at high risk of developing a disseminated infection.

The determination of the reference value S according to the invention is based on a significant sampling of patients, that is to say on a minimum number of samples to obtain statistically relevant results which are therefore representative of the population studied.

Such a determination of a reference value S is widely known to those skilled in the art. It consists especially in implementing an assay method identical to that used in the method of the invention, in biological samples from the two populations studied, and in determining the test value (dose) making it possible to discriminate between these two populations.

The determination of the test value (dose) S making it possible to discriminate between these two populations is known and is calculated using the receiver operating characteristic curve (ROC) curve. This curve is a graph obtained by plotting on the x axis the fraction of false positives, that is to say the specificity as defined below, and on the y axis the fraction of true positives, that is to say the sensitivity as defined below, for different set threshold values. It represents all the sensitivity/specificity pairs when the decision threshold varies over the extent of observed test values. An overall way to quantify the diagnostic effectiveness of a test is to express its performance by the area under the ROC curve. By convention, this area is always ≥0.5. The values of the area under the ROC curve vary between 0.5 (no difference in the distribution of the dosage values between the two subgroups; the ROC curve corresponds to the bisector) and 1 (perfect separation of the dosage values of the two subgroups; the ROC curve passes through the point (0, 1)). The area under the ROC curve is a quantitative expression of the position of the ROC curve with respect to the point (0, 1) (Hanley, J. A. and McNeil, B. J, 1982; Zweig, M. H. and Campbell G., 1993).

Sensitivity represents the percentage of true positives among all the positives, recognized as such. It expresses the ability of the test to detect the truly positive biological samples, which correspond to the pathology. In a "probabilistic" language, it corresponds to the probability of observing a positive result knowing the sample to be positive.

Specificity represents the percentage of true negatives among all the negatives, recognized as such. It expresses the ability of the test to not diagnose as positive those samples which are really negative and which correspond to a healthy individual. In a "probabilistic" language, it corresponds to the probability of observing a negative result knowing the sample to be negative.

To obtain the reference value S, the following conditions must be fulfilled:

the samples taken from the two patient populations preferably originate from patients admitted to intensive care having the same characteristics or a majority of common characteristics, especially of the same sex and/or a similar or identical age and/or the same ethnic origin, with those of the subject or patient in whom it is desired to determine the risk of developing a disseminated infection;

the samples used to obtain the reference value S must be of the same nature as the samples taken from the patient in whom it is desired to predict the risk of developing an infection;

the patients do not have symptoms of disseminated infection at the time of taking the biological sample, and their progression to a disseminated or non-disseminated infection is documented a posteriori.

The method of the present invention makes it possible to draw conclusions regarding the level of risk (high or not) of developing a disseminated infection in the patient from which the biological sample originates, a Δ value lower than said threshold value S meaning that the patient admitted to intensive care is a patient at high risk of developing a disseminated infection, and a Δ value greater than said threshold value S meaning that the patient admitted to intensive care is not a patient at high risk of developing a disseminated infection.

A high-risk patient is as defined above.

According to the result of the method of the invention and the stratification of the patient, if they are considered to be a patient at high risk of developing a disseminated infection, the clinician may decide on one or more of the following actions: administration of prophylactic antibiotic treatment or else targeted immunotherapy, or, more simply, points of entry for pathogens could be limited (i.e. withdrawal of catheters as soon as possible, etc.).

The invention will be better understood with the aid of the following examples which are given by way of non-limiting illustration and with reference to FIGS. 1 to 10, in which.

Figure 7:
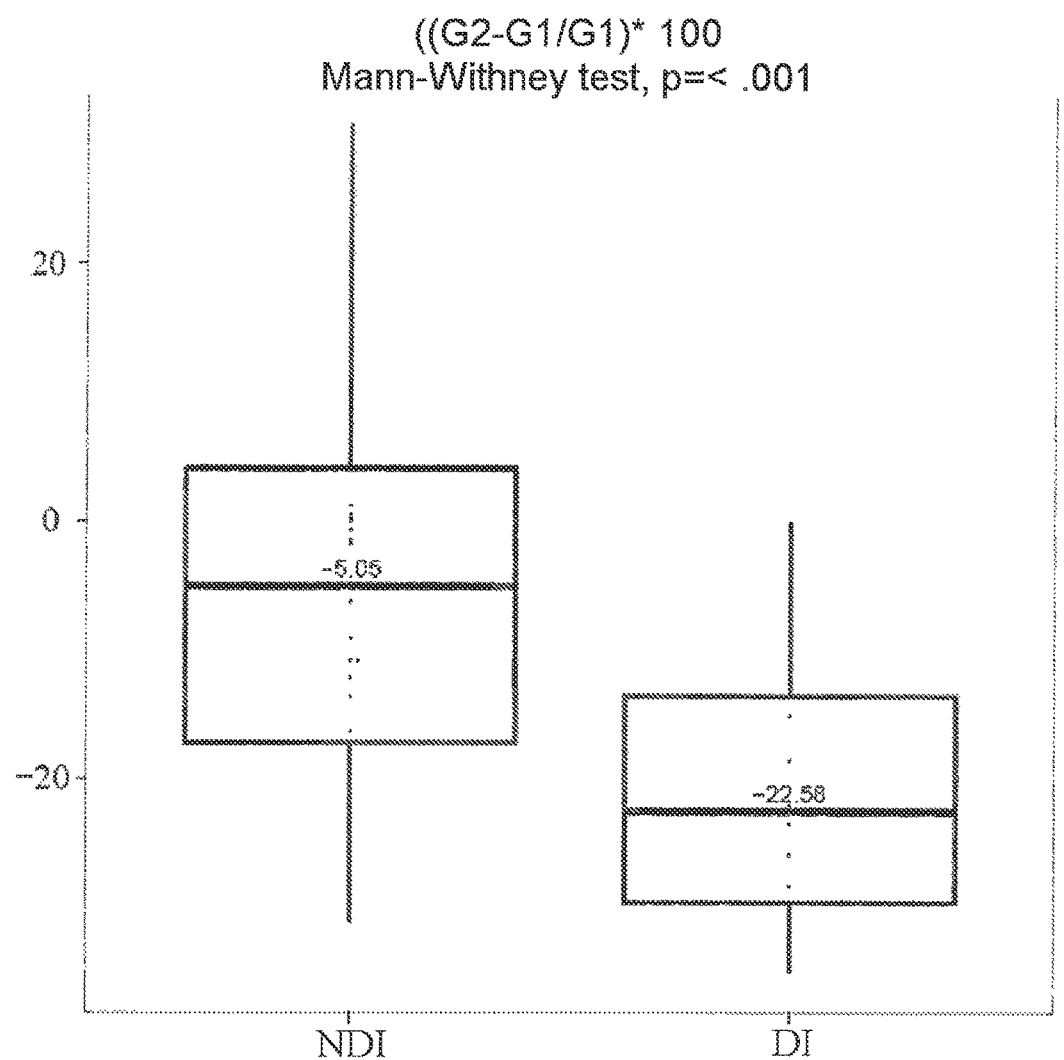
FIG. 7 is a graphical representation giving, on the y axis, the degree of variation $$\frac{G2 - G1}{G1} \times 100$$
Figure 8:
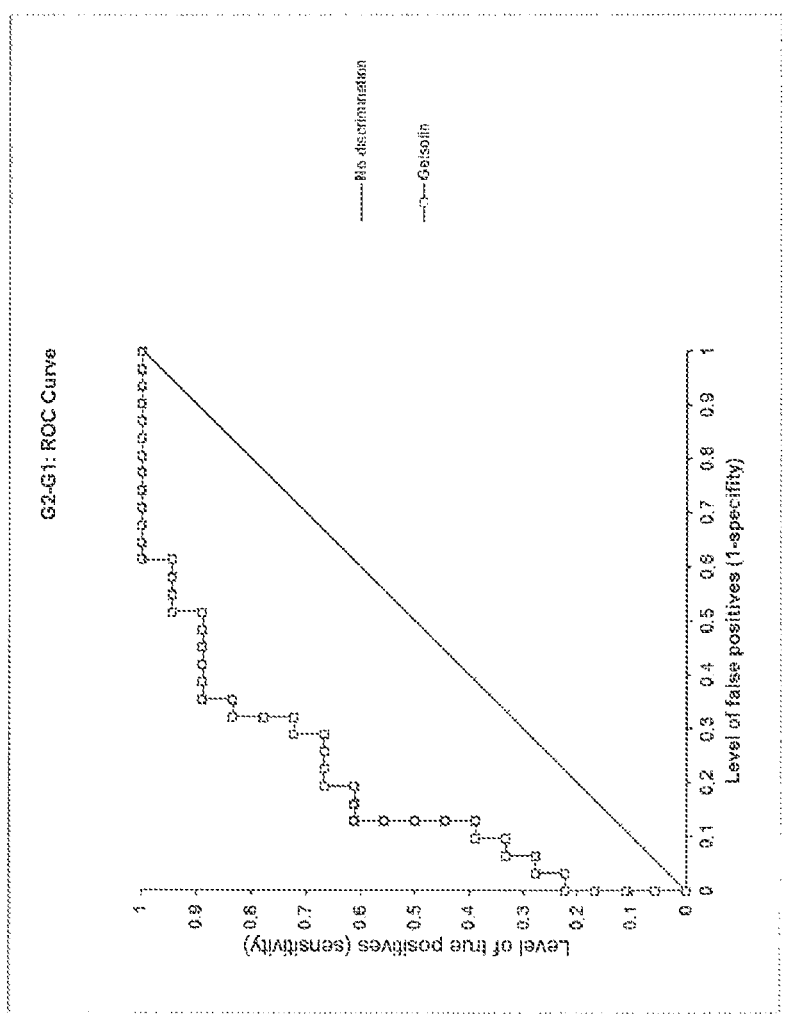
Figure 9:
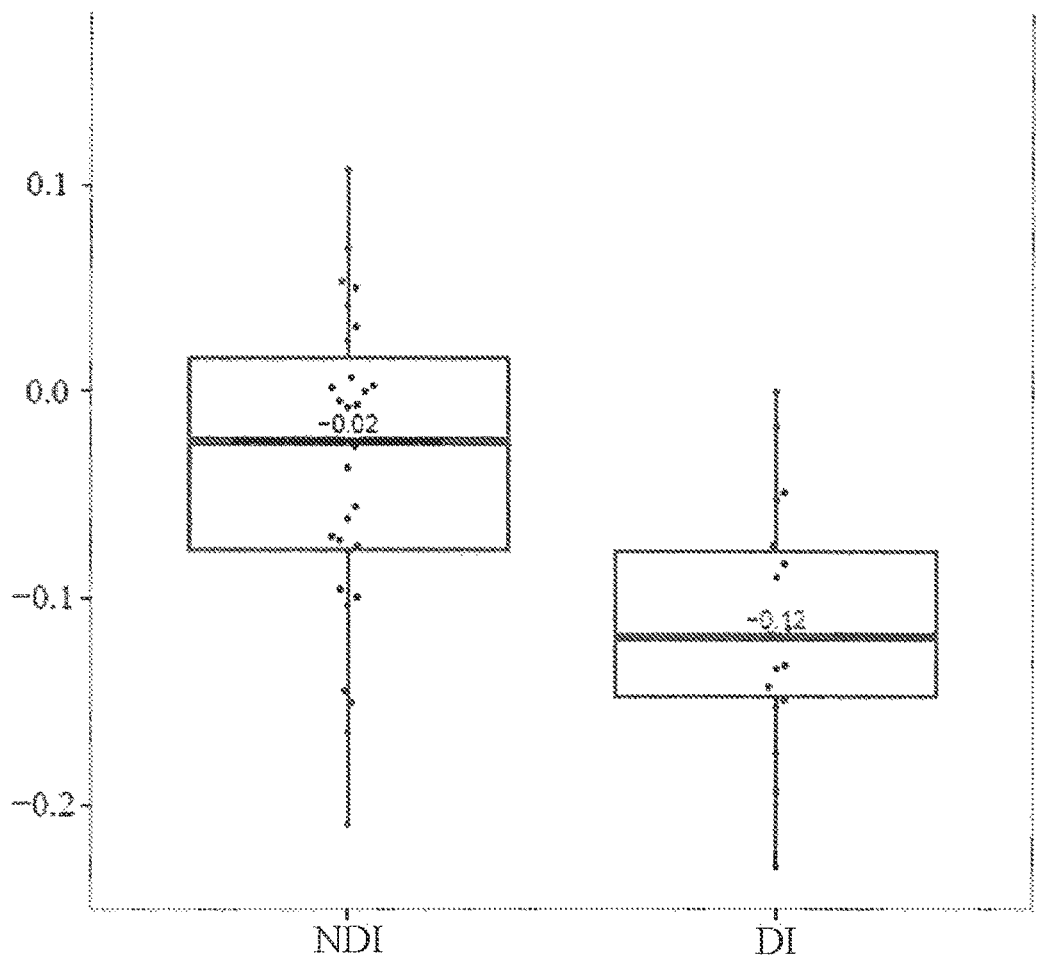
Figure 10:
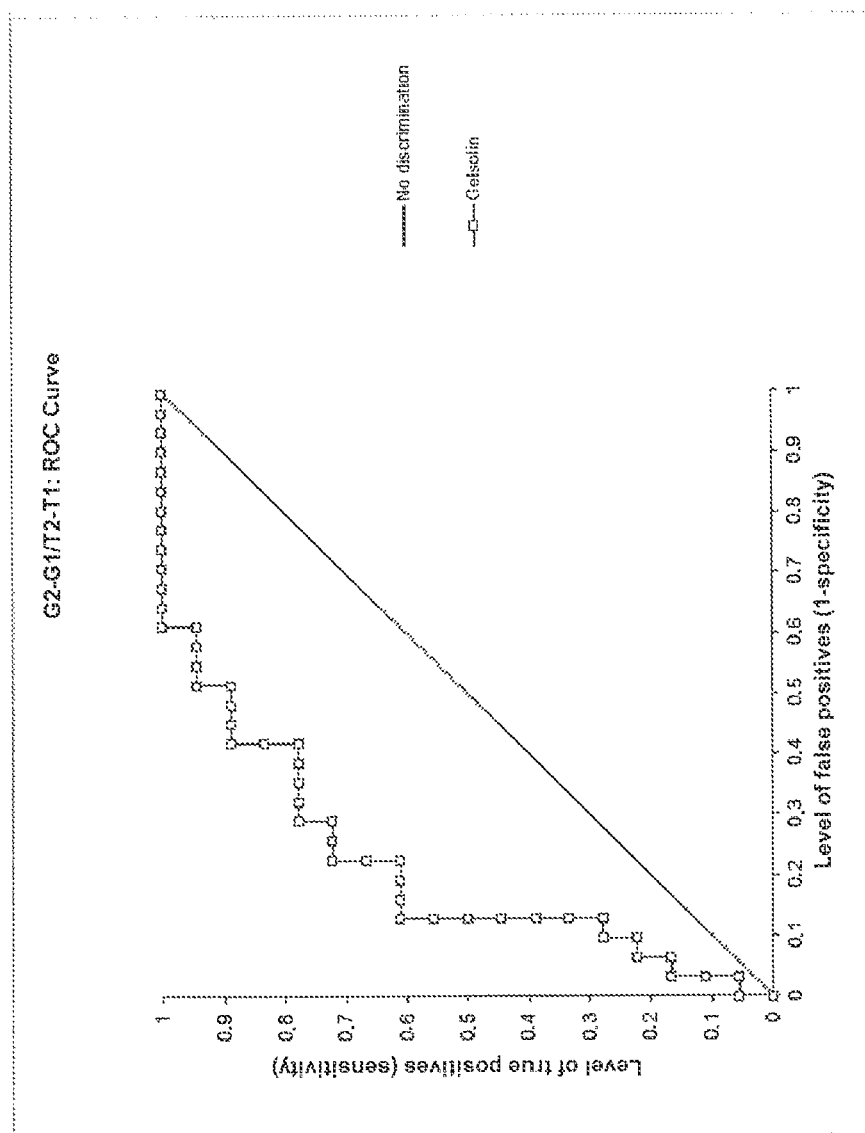

as a function of the status of the group of 49 patients admitted to intensive care, patients whose clinical follow-up showed that they subsequently developed a disseminated infection (DI) and patients whose clinical follow-up showed that they did not subsequently develop such an infection (NDI);

FIG. 8 is an ROC (receiver operating characteristic) curve of the degree of variation $$\frac{G2 - G1}{G1} \times 100,$$

making it possible to choose the threshold value from the results of FIG. 7, to achieve a minimum sensitivity of 75%;

FIG. 9 is a graphical representation giving, on the y axis, the difference in the dose of gelsolin between T2 and T1, corrected by the time interval between the two samplings, according to the following equation $$\frac{G2 - G1}{T2 - T1}$$

in unit of dose per unit of time, as a function of the status of the group of 49 patients admitted to intensive care, patients whose clinical follow-up showed that they subsequently developed a disseminated infection (DI) and patients whose clinical follow-up showed that they did not subsequently develop such an infection (NDI);

FIG. 10 is an ROC (receiver operating characteristic) curve of the difference in dose per unit of time, calculated according to the following equation $$\frac{G2 - G1}{T2 - T1},$$

making it possible to choose the threshold value from the results of FIG. 9, to achieve a minimum sensitivity of 75%.

EXAMPLES

Example 1: Obtaining and Preparing Blood Samples

This retrospective observational study was conducted from 2009 to 2012 in severe multiple-trauma patients admitted to the intensive care unit of the Edouard-Herriot Hospital in Lyon. The criteria for inclusion were the following:
Patients aged 18 years or older
ISS (injury severity score) greater than or equal to 25
Length of stay in intensive care unit estimated at at least 3 days
Under mechanical ventilation
Clinical criteria for exclusion were aspiration pneumonia, intestinal perforation during trauma, immunosuppressive therapy, and death during the first 48 hours.

49 severe multiple-trauma patients were included in the study. All of these patients met the following criteria:
the first blood sample was taken within the first 48 hours following the trauma (T1);
the second blood sample was taken 2 to 3 days after the first (96 to 120 hours after the trauma−T2);
the date on which the primary infection occurred, for the patients concerned, was after the date of the second sampling.

Of these patients, 18 developed a disseminated infection (septic syndrome), on average 5 days after their admission to intensive care.

Two blood samples were taken on EDTA tubes for each patient included in the study, according to the supplier's recommendations. The tubes were then gently agitated by turning for 15 minutes before being centrifuged for 15 minutes at 2750 g and at 15° C. The supernatants were taken off gently and then frozen at −80° C. until the gelsolin was assayed.

Example 2: Detection of Gelsolin by LC-MS Technique

The successive steps of the SRM analysis method are:
1) enzymatic digestion,
2) SPE (solid-phase extraction) fractionation of the peptides,
3) liquid chromatography (LC) coupled to MS.

Nevertheless, before carrying out this method, the various parent ion/fragmentation ion pairs, or SRM transitions, were identified as follows:

From the complete sequence of isoform 1 of secreted gelsolin (SEQ ID NO: 1) obtained in Uniprot (Swissprot No. P06396-1), the list of theoretical SRM transitions of the 3 selected proteotypic peptides of sequences SEQ ID NOs. 2 to 4 for assaying the gelsolin marker was generated using the Skyline software (Brendan MacLean et al., 2010). This software makes it possible to carry out a fictitious trypsin digestion of the protein from its peptide sequence in order to generate a theoretical list of peptides. From this list of peptides, the SRM transitions of all the doubly charged or triply charged parent ions of the theoretical tryptic peptides in a mass range extending from 400 to 1000 Da and all the possible fragment ions of y or b type were predicted.

SEQ ID NO. 1: isoform 1 of gelsolin
MAPHRPAPALLCALSLALCALSLPVRAATASRGASQAGAPQGRVPEAR -continued

PNSMVVEHPEFLKAGKEPGLQIWRVEKFDLVPVPTNLYGDFFTGDAYV

ILKTVQLRNGNLQYDLHYWLGNECSQDESGAAAIFTVQLDDYLNGRAV

QHREVQGFESATFLGYFKSGLKYKKGGVASGFKHVVPNEVVVQRLFQV

KGRRVVRATEVPVSWESFNNGDCFILDLGNNIHQWCGSNSNRYERLKA

TQVSKGIRDNERSGRARVHVSEEGTEPEAMLQVLGPPALPAGTEDTAK

EDAANRKLAKLYKVSNGAGTMSVSLVADENPFAQGALKSEDCFILDHG

KDGKIFVWKGKQANTEERKAALKTASDFITKMDYPKQTQVSVLPEGGE

TPLFKQFFKNWRDPDQTDGLGLSYLSSHIANVERVPFDAATLHTSTAM

AAQHGMDDDGTGQKQIWRIEGSNKVPVDPATYGQFYGGDSYIILYNYR

HGGRQGQIIYNWQGAQSTQDEVAASAILTAQLDEELGGTPVQSRVVQG

KEPAHLMSLFGGKPMIIYKGGTSREGGQTAPASTRLFQVRANSAGATR

AVEVLPKAGALNSNDAFVLKTPSAAYLWVGTGASEAEKTGAQELLRVL

RAQPVQVAEGSEPDGFWEALGGKAAYRTSPRLKDKKMDAHPPRLFACS

NKIGRFVIEEVPGELMQEDLATDDVMLLDTWDQVFVWVGKDSQEEEKT

-continued

EALTSAKRYIETDPANRDRRTPITVVKQGFEPPSFVGWFLGWDDDYWS

VDPLDRAMALAA

The proteotypic peptides selected for gelsolin from the sequence SEQ ID NO. 1 are HVVPNEVVVQR (SEQ ID NO: 2), AGALNSNDAFVLK (SEQ ID NO: 3), and QTQVSVLPEGGETPLFK (SEQ ID NO: 4).

The 3 proteotypic peptides selected were then synthesized chemically and infused directly into the mass spectrometer in order to select the most intense transitions and to optimize, for each of them, the parameters of the spectrometer:
the collision energy (CE),
the orifice voltage (DP, declustering potential)
the enhanced potential (EP) and
the voltage at the outlet of the collision cell (CXP, collision cell exit potential).

Figure 1:
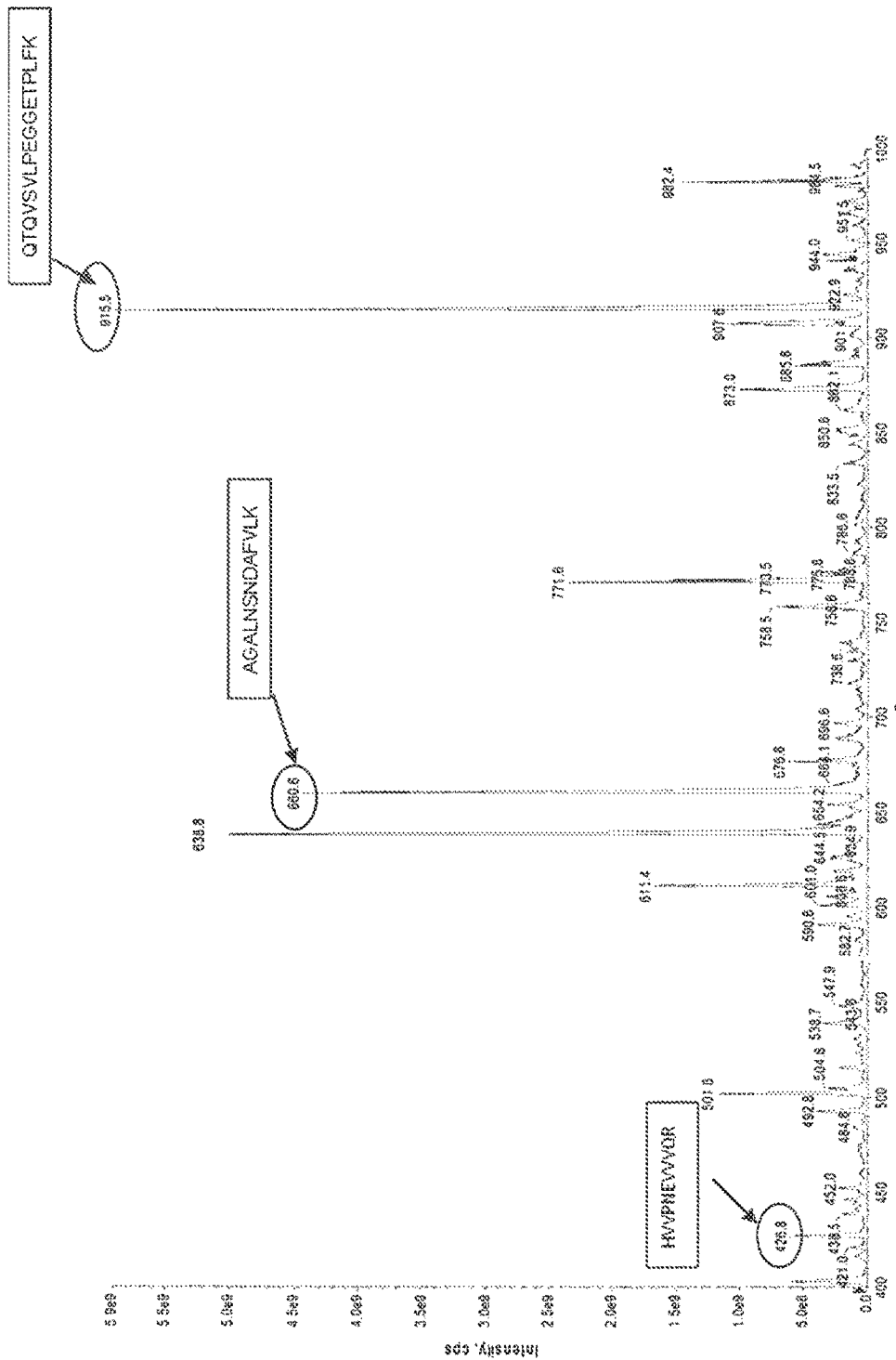
FIG. 1 represents a graph giving the MS spectrum, in enhanced mass spectrometry (EMS) mode, of three synthetic proteotypic peptides of the gelsolin protein for the selection of molecular ions (parent ions), the x axis being the m/z ratio in Dalton and the y axis the intensity in counts per second (cps), on which the three proteotypic peptides used appear.
Figure 2:
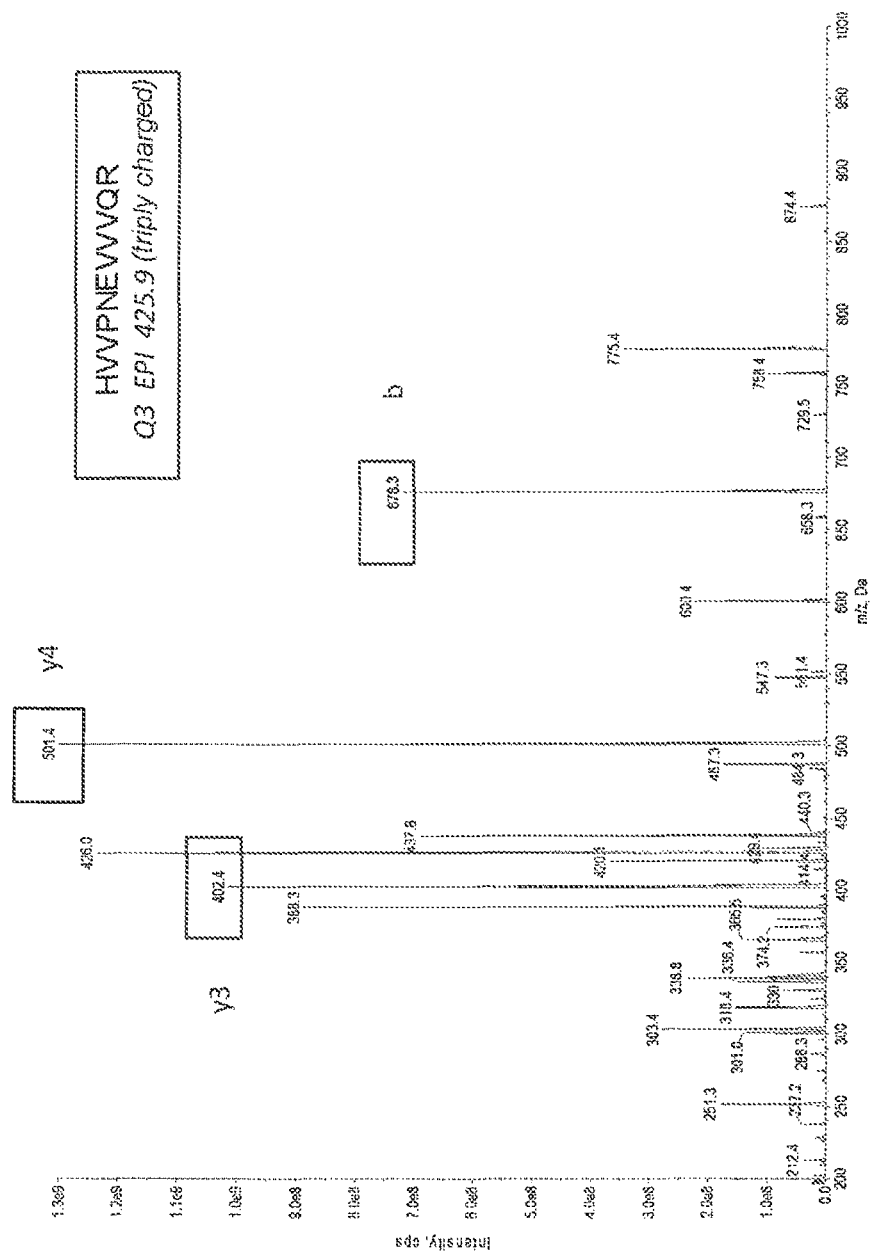
FIG. 2 represents a graph giving the MS spectrum in enhanced product ion (EPI) mode for the selection of the fragment ions obtained from the parent ion selected for the peptide HVVPNEVVVQR, the x axis being the m/z ratio in Dalton and the y axis the intensity in counts per second (cps).
Figure 3:
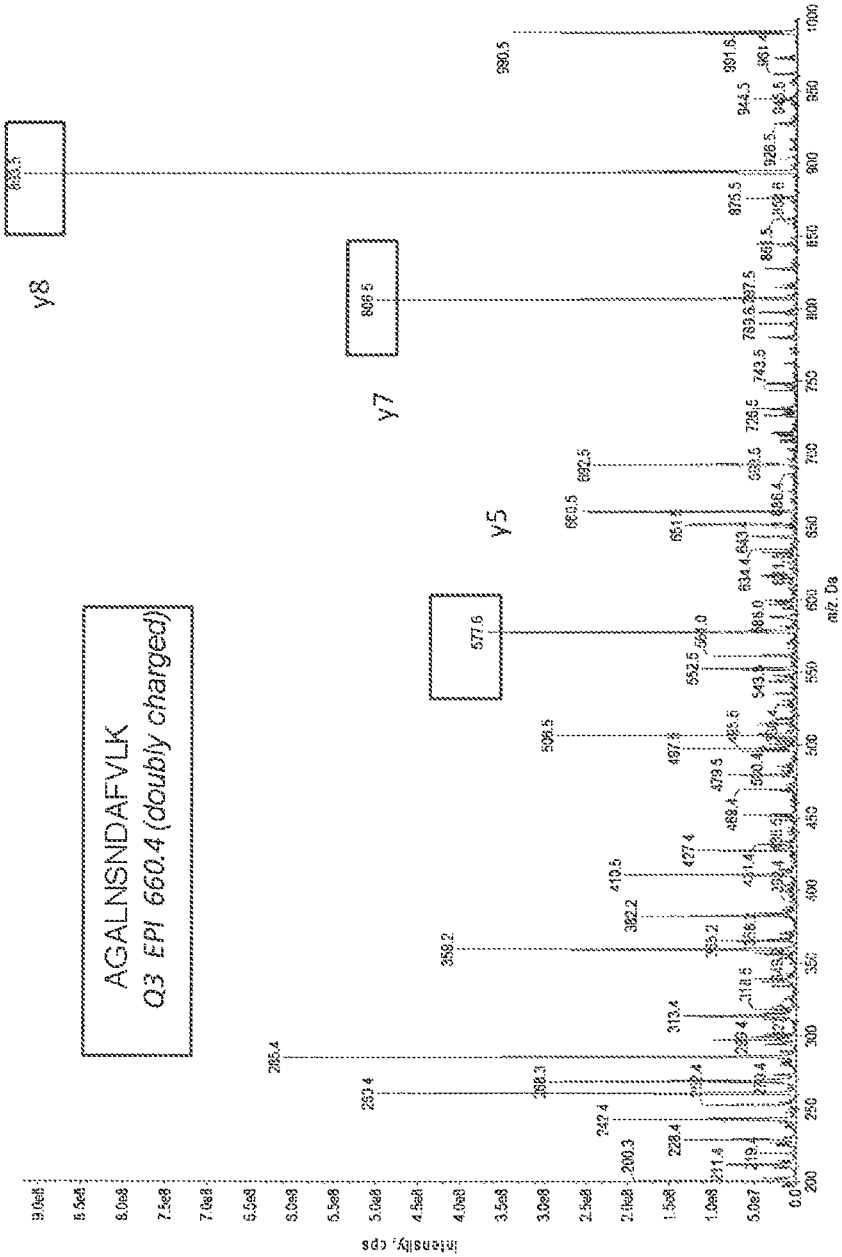
FIG. 3 represents a graph giving the MS spectrum in enhanced product ion (EPI) mode for the selection of the fragment ions obtained from the parent ion selected for the peptide AGALNSNDAFVLK, the x axis being the m/z ratio in Dalton and the y axis the intensity in counts per second (cps).
Figure 4:
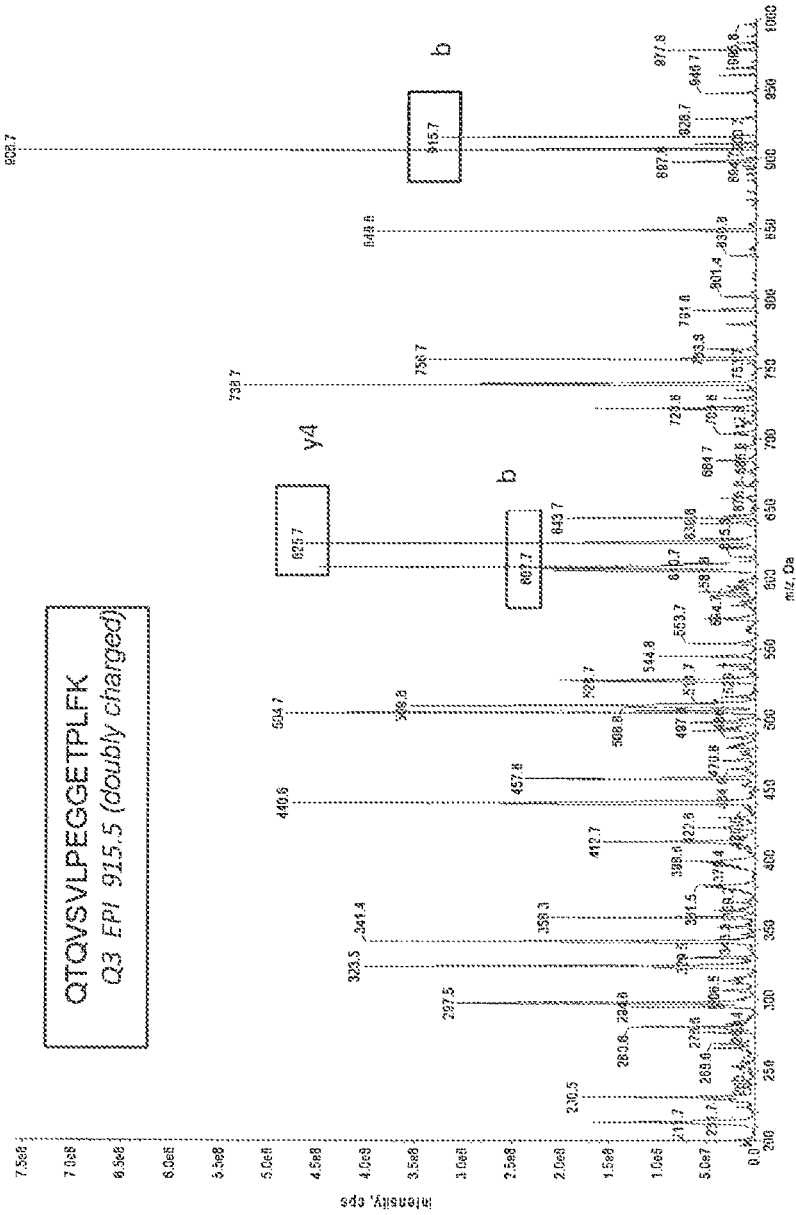
FIG. 4 represents a graph giving the MS spectrum in enhanced product ion (EPI) mode for the selection of the fragment ions obtained from the parent ion selected for the peptide QTQVSVLPEGGETPLFK, the x axis being the m/z ratio in Dalton and the y axis the intensity in counts per second (cps).

The mass spectra in EMS (enhanced mass spectrometry) mode for selecting parent ions are represented in FIG. 1 and those in EPI (enhanced product ion) mode for selecting fragmented ions selected from the parent ions HVVPNEVVVQR, AGALNSNDAFVLK and QTQVSVLPEGGETPLFK are shown in FIGS. 2 to 4, respectively.

The result of this selection is summarized in table 1.

TABLE 1

| Sequences (SEQ ID NO.) | pI | TR | Elution fraction | Q1 (natural light peptide) | Q3 (natural light peptide) | Q1 (heavy internal standard peptide) | Q3 (heavy internal standard peptide) | DP | EP | CE | CXP |
|---|---|---|---|---|---|---|---|---|---|---|---|
| HVVPNEVVVQR (SEQ ID NO: 2) | 5.9 | 10.1 | F5-8 | 425.9 | 402.2 | 429.2 | 412.2 | 30 | 11 | 21 | 11 |
|  |  |  |  |  | 501.3 |  | 511.3 | 30 | 11 | 19 | 12 |
|  |  |  |  |  | 676.3 |  | 676.3 | 30 | 11 | 17 | 16 |
| AGALNSNDAFVLK (SEQ ID NO: 3) | 5.88 | 15.5 | F5 | 660.4 | 577.4 | 664.4 | 585.4 | 64 | 12 | 40 | 14 |
|  |  |  |  |  | 806.5 |  | 814.5 | 64 | 12 | 32 | 19 |
|  |  |  |  |  | 893.5 |  | 901.5 | 64 | 12 | 32 | 21 |
| QTQVSVLPEGGETPLFK (SEQ ID NO: 4) | 4.53 | 21.3 | F5 | 915.5 | 457.2 | 919.5 | 457.2 | 31 | 3.5 | 40 | 12 |
|  |  |  |  |  | 504.3 |  | 512.3 | 31 | 3.5 | 57 | 12.5 |
|  |  |  |  |  | 756.4 |  | 756.4 | 31 | 3.5 | 37 | 18 |

1) Enzymatic Digestion:

The plasma samples (volume 100 µl overloaded with 20 µl of synthetic heavy peptides) obtained in example 1 are denatured and reduced in a 6 M urea solution buffered with ammonium bicarbonate (pH 8, 5 mM) and containing 15 mM dithiothreitol, for 40 minutes at 60° C., then alkylated with 35 mM iodoacetamide at room temperature for 40 minutes in the dark. The samples are then diluted 8 times with 50 mM ammonium bicarbonate buffer, pH 8, before being digested for 4 hours at 37° C. with 200 µg of trypsin (Sigma). A second reduction-alkylation cycle is carried out before a second trypsin digestion step carried out at 37° C. overnight.

2) SPE Fractionation:

The digested samples are sonicated with ultrasound for 15 minutes and centrifuged for 30 minutes at 15 000 g. They are then loaded onto 60 mg mixed (hydrophobic and ion-exchange) Oasis MCX (mixed cation exchange) and Oasis MAX (mixed anion exchange) cartridges (Waters). The samples loaded onto the MCX cartridges are acidified beforehand with a pH 3 solution composed of water/2% formic acid. The samples loaded onto the MAX cartridges are basified beforehand with a pH 12 solution composed of water/10% ammonium hydroxide. The cartridges are equilibrated beforehand with methanol.

The fractionation procedure is described in table 2 below:

TABLE 2

| STEPS | Function | MCX | MAX |
|---|---|---|---|
| Conditioning | Activation of the adsorbent | $H_2O$/2% AF pH = 3 | $H_2O$/10% NH3 pH = 12 |
| Sample deposition | Fixation of peptides of interest Elimination of salts | Volume = 5.5 ml | Volume = 5.5 ml |
| Washes | Contaminant elimination | H2O/2% AF pH = 3 | H2O/10% NH3 pH = 12 |
| Elution 1 = MCX-F5 or MAX F8 fraction | Elution of peptides of interest Concentration of sample | 50% methanol/50% pH 5 buffer (V/V) | 50% methanol/50% pH 8 buffer (V/V) |
| Elution 2 = MCX-F5-8 or MAX F8-4 fraction | Elution of peptides of interest Concentration of sample | 50% methanol/50% pH 8 buffer (V/V) | 50% methanol/50% pH 4 buffer (V/V) |
| Elution 3 = MCX-F5-8-12 or MAX F8-4-3 fraction | Elution of peptides of interest Concentration of sample | 90% methanol/10% pH 12 buffer (V/V) | 80% methanol/20% pH 3 buffer (V/V) |

The peptides to be assayed are eluted with 1 ml of a methanol/ammonium bicarbonate buffer (v/v) mixture. The pH of the bicarbonate buffer is chosen as a function of the isoelectric point of the proteotypic peptide of interest. The eluates are partially evaporated under a stream of nitrogen using a TurboVap® system (Biotage) and then the volume is adjusted to obtain a volume of 250 μl using a water solution containing 0.5% formic acid.

3) Liquid Chromatography (LC and Mass Spectrometry (MS):

A 100 μl aliquot is injected into the LC coupled to an MS system according to the following characteristics.

The LC-MS analysis is performed on a high-pressure chromatography system (HPLC) of Nexera LC type (Shimadzu) with binary pump and injector coupled to a mass spectrometer, AB Sciex 5500 QTrap (triple quadrupole—ion trap hybrid MS) operating in SRM mode (Q1q2Q3). The LC separation is carried out on a 2.1×150 mm C18 reversed-phase column, 3.6 μm (Aeris Peptide, Phenomenex) at an elution rate of 250 μl/min. Eluent A=0.1% formic acid in water, eluent B=0.1% formic acid in methanol. An isocratic gradient at 5% solvent B was produced for 2 min, then a linear gradient of 5% B to 60% B in 37 min, followed by an isocratic gradient at 5% solvent B in 2 min. The MS analysis is carried out in positive ESI (electrospray ionization) mode at a voltage of 5500 V applied to the needle allowing ionization in the source. The flow rates of the nebulizing gas (air) and the curtain gas (nitrogen) are 40 and 50 psi, respectively. The Turbo VTM ion source is set at 550° C., the auxiliary nitrogen flow at 40 psi.

Instrument control and data acquisition are performed with the Analyst 1.5.2 software.

A Schedule-SRM acquisition method was constructed for each fraction using the specific parameters of each transition (DP, EP, CE, CXP, and retention time). A window of 4 min around the retention time of each peptide observed during the tests with the serum and plasma samples overloaded with synthetic peptides and a target scan time of 1.15 seconds were used for all the data acquisitions.

The SRM raw data was reprocessed using the Multiquant 2.1 software (AB Sciex) and the Signal Finder integration algorithm. The software allows the extraction of a chromatogram corresponding to each peptide.

For the calibration, synthetic heavy peptides with sequences identical to the selected target peptides (daughter ions) were synthesized, with labeled lysine or arginine ($^{13}C$ and $^{15}N$): +8 Dalton for lysine, +10 Dalton for arginine, in order to be able to be used as internal standards. The samples were overloaded with these labeled heavy peptides.

For all selected transitions (table 2) corresponding to the peptides of SEQ ID NO: 2, SEQ ID NO: 3, SEQ ID NO: 4, the ratio of the areas of the chromatographic peak of the natural transition divided by the area of the heavy transition was determined to obtain a relative dose per transition for each sample. The relative doses of each transition of the same sample were then compiled together to obtain a single dose representative of the concentration of the protein in the biological sample studied. "Compiled" is intended to mean several independent but correlated doses of the same protein combined together to obtain a single dose per protein. This compilation was carried out by taking the median of the ratios.

Example 3: Statistical Analysis of Data

Patients were divided into 2 groups:
Patients whose clinical status showed that they had not developed a disseminated infection ("NDI"): N=31
Patients whose clinical status showed that they had developed a disseminated infection ("DI"): N=18

A univariate and multivariate logistic regression analysis was performed to identify the variables associated with the risk of infection by determining the odds ratios (ORs) and the associated confidence intervals (95% CIs).

The ROC (receiver operating characteristic) curve and the areas under the curve (AUC: Area Under Curve) were calculated for the Δ values G2–G1

$$\frac{G2-G1}{G1} \times 100 \text{ and } \frac{G2-G1}{T2-T1}.$$

The statistical analysis of the data was performed using the R-3.0.0 language.

Results

Association Between the Dose of Plasma Gelsolin in Patients Admitted to Intensive Care and the Occurrence of a Disseminated Infection.

The association of the gelsolin variable and other clinical variables with the patient's status (in this case "developed a disseminated infection") was tested by means of logistic regression. The strength of the association was estimated with the odds ratios (ORs) calculation, which is the ratio of the probability of developing a disseminated infection to the probability of not developing a disseminated infection.

The clinical variables studied are: sex, trauma severity score (ISS: Injury Severity Score), simplified severity index (SSI II), neurological trauma, pneumological trauma, transfusion of red blood cells, transfusion of frozen fresh plasma.

The gelsolin dose variable was measured according to the method described above by determining the difference in the level of gelsolin G2–G1 between T2 and T1.

For each qualitative variable: neurological trauma, pneumological trauma, transfusion of red blood cells and transfusion of frozen fresh plasma, the odds ratio is interpreted as follows:

OR=1: no association
OR<1: the risk of developing a disseminated infection is more common for patients who do not have this characteristic
OR>1: the risk of developing a disseminated infection is more common for patients who have this characteristic.

For each sex variable, the odds ratio is interpreted as follows:

OR=1: no association
OR<1: the risk of developing a disseminated infection is more common for women
OR>1: the risk of developing a disseminated infection is more common for men.

For each quantitative variable: difference in the level of gelsolin G2–G1, ISS and SSI II, the odds ratio is interpreted as follows:

OR=1: no association
OR<1: an increase from the 1st to the 3rd quartile is associated with a decreased risk of developing a disseminated infection
OR>1: an increase from the 1st to the 3rd quartile is associated with an increased risk of developing a disseminated infection.

All of these variables were monitored in patients admitted to intensive care who developed a disseminated infection in the days following their admission.

Univariate logistic regressions were performed for each of these covariables. Then, the variables with a p-value less than 0.1 in the univariate analysis were retained in the multivariate analysis, which led to the determination of the adjusted odds ratios.

The results are given in table 3 below.

The results in table 3 show that the difference in the dose of plasma gelsolin measured at two or three days of interval (T2–T1) was significantly associated with the patient's status ("developed a disseminated infection") and thus with the risk of developing a disseminated infection. Indeed, univariate logistic regression analyses determined an odds ratio of 0.11 for the difference in gelsolin between T2 and T1 and of 0.1 in multivariate analysis, with a p-value of 0.0013 and 0.002, respectively, as shown in table 3. Moreover, the other variables are not significant in the multivariate analysis.

A patient with a difference in gelsolin G2–G1 of −0.288 has a 10 times greater risk of developing a disseminated infection than a patient with a difference in gelsolin G2–G1 of −0.002.

Prediction of the Occurrence of a Disseminated Infection by Measuring the Dose of Plasma Gelsolin Beyond the association between the dose of plasma gelsolin and the risk of developing a disseminated infection, our study showed that the difference in the dose of plasma gelsolin measured in two successive samples taken with an interval of two or three days enabled prediction of the occurrence of a disseminated infection in the days that followed (<D8).

$\Delta$ Value=$G2-G1$

The results of the difference G2–G1 for the 49 patients are given in FIG. 5, giving, on the y axis, the difference G2–G1 in unit of dose, as a function of a group of 49 patients admitted to intensive care, patients whose clinical follow-up showed that they subsequently developed a disseminated infection (DI) and patients whose clinical follow-up showed that they did not subsequently develop such an infection (NDI).

Figure 5:
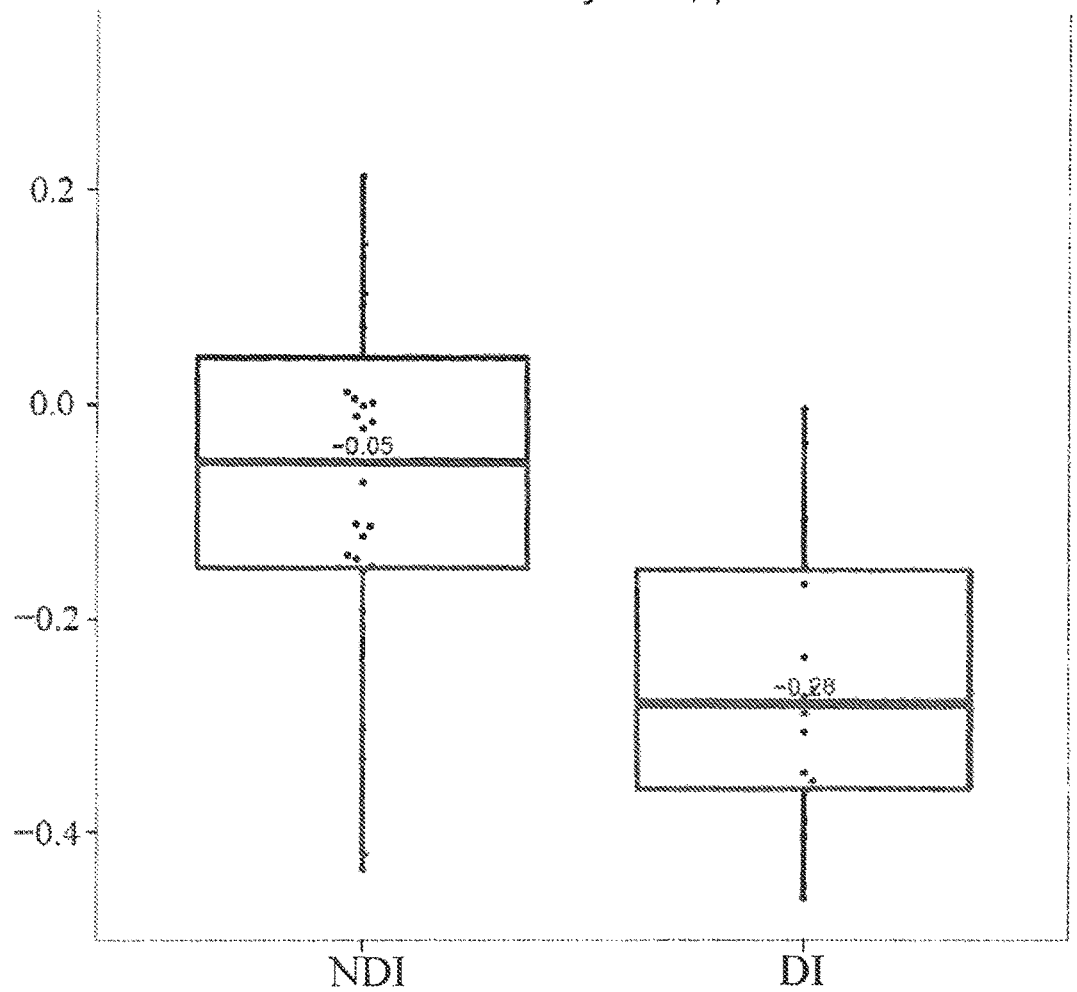
FIG. 5 is a graphical representation giving, on the y axis, the difference G2−G1 in unit of dose, as a function of a group of 49 patients admitted to intensive care, patients whose clinical follow-up showed that they subsequently developed a disseminated infection (DI) and patients whose clinical follow-up showed that they did not subsequently develop such an infection (NDI)

The results in FIG. 5 show that the dose of gelsolin between the two samplings always decreases (G2–G1<0) for patients who will develop a disseminated infection in the following days and that this decrease is significantly more marked in this population compared to patients who will not develop a disseminated infection.

Figure 6:
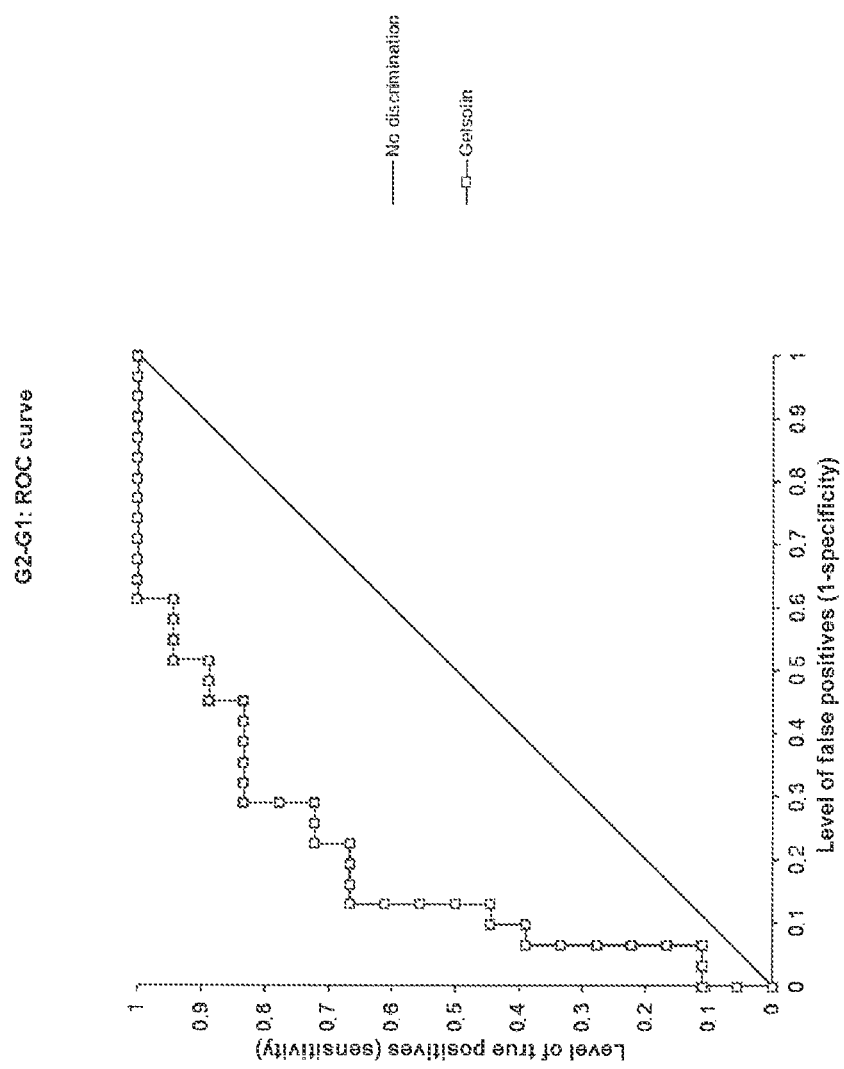
FIG. 6 is an ROC (receiver operating characteristic) curve of the difference G2−G1, making it possible to choose the threshold value from the results of FIG. 5, to achieve a minimum sensitivity of 75%.

The determination of a threshold value to enable prediction between patients at high risk of developing a disseminated infection and patients who are not at high risk, based on the $\Delta$ value obtained using the equation G2–G1, was carried out using the ROC curve as given in FIG. 6. Thus, taking a set threshold value of −0.144839402777984 (negative value), it is possible to predict, in patients having a $\Delta$ value below this threshold value, the occurrence of an infection in the following days, with a sensitivity of 83.3% and a specificity of 71%.

TABLE 3

| Variables | Univariate analysis | | | Multivariate analysis | | | |
|---|---|---|---|---|---|---|---|
| | OR | 95% CI | P-value | OR | 95% CI | | P-value |
| Sex (male) | 2.21 | 0.59 8.32 | 0.2408 | | | | |
| ISS (34-50) | 0.99 | 0.93 1.05 | 0.9869 | | | | |
| SSI II (33-58) | 2.56 | 2.46 2.67 | 0.0797 | 3.60 | 0.13 | 99.73 | 0.0633 |
| Neurotrauma (yes) | 3.17 | 0.94 10.70 | 0.0635 | 3.74 | 1.00 | 1.11 | 0.0893 |
| Pneumological trauma (yes) | 0.38 | 0.10 1.38 | 0.1417 | | | | |
| Red blood cell transfusion (yes) | 1.82 | 0.18 18.95 | 0.6158 | | | | |
| Frozen fresh plasma transfusion (yes) | 1.43 | 0.37 5.55 | 0.6036 | | | | |
| Gelsolin G2-G1 (−0.288-(−0.002)) | 0.11 | 0.001 12.33 | 0.0013 | 0.10 | 0.02 | 0.46 | 0.0021 |

$$\Delta \text{ Value} = \frac{G2 - G1}{G1} \times 100$$

The result was also expressed in relative variability by the calculation of the rate of change, according to equation (II), as follows $$\frac{G2 - G1}{G1} \times 100.$$

The results are given in FIG. 7, which shows the median value for patients who will be subject to a disseminated infection; this median value is −22% (the dose of gelsolin decreases by 22% (median) between T1 and T2 in these patients, compared with 5.05% in patients who will not contract an infection).

A threshold value was determined with this cohort when the Δ value for the equation $$\frac{G2 - G1}{G1} \times 100$$

using the ROC curve, as shown in FIG. 8. Thus, taking a set threshold value equal to −0.121558271983808, it is possible to predict, in patients having a Δ value lower than this threshold value, the occurrence of a disseminated infection in the following days with a sensitivity of 83.3% and a specificity of 67.7%.

It can be concluded therefrom that, with this dataset, this method is not the most appropriate, but this does not limit the use of such a method with a larger cohort of patients.

$$\Delta \text{ Value} = \frac{G2 - G1}{T2 - T1}$$

On the other hand, in order to take into account the time interval between the two samplings, which is not always homogeneous from one patient to another, we investigated the variation in the level of gelsolin per day by calculating the ratio of the difference in gelsolin over the time interval between the 2 samplings. This calculation consisted in calculating the ratio of the difference in gelsolin over the time interval between the two samplings according to equation (III); as follows:

$$\frac{G2 - G1}{T2 - T1}$$

The results are shown in FIG. 9. With this calculation, we showed that the median difference in the dose of gelsolin per day is −0.02 in patients who will not develop a disseminated infection, while it is −0.12 in patients who will develop a disseminated infection.

A threshold value was determined when the Δ value for the equation $$\frac{G2 - G1}{T2 - T1}$$

using the ROC curve, as shown in FIG. 10. Thus, taking a set threshold value equal to −0.072419701388992, it was possible to predict the occurrence of a disseminated infection in the days that followed with a sensitivity of 77.8% and a specificity of 71%.

It can be concluded therefrom that, with this dataset, this method is not the most appropriate, but this does not limit the use of such a method with a larger cohort of patients.

According to the data with the 49 patients, it is the first method (Δ value=G2−G1) which makes it possible to have the best compromise. Nonetheless, the other methods for calculating the Δ value remain suitable for other data with a larger cohort.

Surprisingly, our study showed that the measurement of the level of plasma gelsolin in two successive samplings, performed within the first 48 hours following admission for the first, and then two to three days later for the second, made it possible to predict, in the absence of clinical signs indicating a disseminated infection, the occurrence of a disseminated infection in patients admitted to intensive care.

LITERATURE REFERENCES

Ali Y M et al., 2014, Low-dose recombinant properdin provides substantial protection against *Streptococcus pneumonia* and *Neisseria meningitidis* infection, Proc Natl Acad Sci U.S.A, 111(14):5301-6

Asehnoune K et al., 2014, Hydrocortisone and fludrocortisone for prevention of hospital-acquired pneumonia in patients with severe traumatic brain injury (Corti-TC): a double-blind, multicenter phase 3, randomized placebo-controlled trial, Lancet Respir Med, 2:706-16

Bone R. C. et al., 1992, the ACCP/SCCM Consensus Conference Committee. American College of Chest Physicians/Society of Critical Care Medicine, Chest, 101 (6):1644-1655

Brendan MacLean et al., 2010, BIOINFORMATICS, Vol. 26 no. 7: 966-968

Bucki R. et al., 2005, Inactivation of Endotoxin by Human Plasma Gelsolin, Biochemistry, 44 (28)

Chahin A et al., 2015, The novel immunotherapeutic oligodeoxynucleotide IMT504 protects neutropenic animals from fatal *Pseudomonas aeruginosa* bacteriemia and sepsis, Antimicrob Agents Chemother, 59(2):1225-9

Eggiman P et al., 2001, Infection control in the ICU, Chest, 120(6):2059-93

Essader A S, et al., 2005, A comparison of immobilized pH gradient isoelectric focusing and strong-cation-exchange chromatography as a first dimension in shotgun, Proteomics, 5, 24-34

Fortin T. et al., 2009, Clinical Quantitation of Prostate-specific Antigen Biomarker in the Low Nanogram/Milliliter Range by Conventional Bore Liquid Chromatography-Tandem Mass Spectrometry (Multiple Reaction Monitoring) Coupling and Correlation with ELISA Tests. Mol. Cell Proteomics, 8(5): 1006-1015.

Hanley, J. A. and McNeil, B. J., 1982, The meaning and use of the area under a receiver operating characteristic (ROC) curve, Radiology, 143: 29-36.

Jensen J U et al., 2011, Procalcitonin-guided interventions against infections to increase early appropriate antibiotics and improve survival in the intensive care unit: a randomized trial, Crit Care Med, 39(9):2048-58

Lambert M L S C et al., 2011, Clinical outcomes of health-care-associated infections and antimicrobial resistance in patients admitted to european intensive-care units: a cohort study, Lancet Infect Dis, 11:30-8

Lee P S, et al., 2008, Plasma gelsolin depletion and circulating actin in sepsis: a pilot study. PLoS One. 2008; 3(11):e3712.

Li G H, et al., 2012, Multifunctional roles of gelsolin in health and diseases. Med Res Rev. 2012 September; 32(5):999-1025

Michel P E, et al., 2003, Protein fractionation in a multi-compartment device using Off-Gel, isoelectric focusing, Electrophoresis, 24, 3-11

Oschsner U. A. et al., 2014, Systematic selection of modified aptamer pairs for diagnostic sandwich assays, BioTechniques, 56: 125-133

Puisieux F, et al., 1993, Prophylactic antibiotherapy using cefapirin in the surgery of duodenal ulcer: a randomized clinical trial, Ann Fr Anesth Reanim, 12(3):289-92

Vincent J L, 2003, Nosocomial infections in adult intensive-care units, Lancet, 361(9374):2068-77

Wang H, et al., 2008, Time course of plasma gelsolin concentrations during severe sepsis in critically ill surgical patients. Crit Care. 2008; 12 (4): R106.

Xianhui L. et al., 2014, *The association between plasma gelsolin level and prognosis of burn patients*. Burns, vol. 40, no. 8, pages 1552-1555

Zweig, M. H. and Campbell G., 1993, Receiver-Operating Characteristic (ROC) Plots: a fundamental evaluation tool in clinical medicine, Clin. Chem., 39/4: 561-577

The invention claimed is:

1. A method for predicting the risk of developing a disseminated infection in a patient admitted to intensive care having no clinical symptoms of such an infection, comprising the following steps:
   determining a first dose of gelsolin G1 in a biological sample from said patient originating from a first sample taken at the time T1, carried out between the day of admission to intensive care and 48 hours afterward,
   determining a second dose of gelsolin G2 in a biological sample from said patient originating from a second sample taken at the time T2, carried out two to three days after the first sampling,
   calculating the variation between the dose of gelsolin G2 and the dose of gelsolin G1, giving a Δ value,
   comparing the Δ value obtained in the preceding step to a threshold value S determined beforehand from two populations of patients admitted to intensive care, one not having developed a disseminated infection and the other having developed such an infection,
   a Δ value lower than said threshold value S meaning that the patient admitted to intensive care is a patient at high risk of developing a disseminated infection, and
   a Δ value greater than said threshold value S meaning that the patient admitted to intensive care is not a patient at high risk of developing a disseminated infection.

2. The method as claimed in claim 1, wherein the Δ value is calculated according to the following formula (I):
$$G2-G1 \tag{I}$$

3. The method as claimed in claim 1, wherein the Δ value corresponds to the relative rate of change and is calculated according to the following formula (II):

$$\frac{G2-G1}{G1} \times 100. \qquad (II)$$

4. The method as claimed in claim 1, wherein the Δ value corresponds to the difference in dose per unit time and is calculated according to the following formula (III):

$$\frac{G2-G1}{T2-T1}. \qquad (III)$$

5. The method as claimed in claim 1, wherein the first sampling (T1) is performed on the day of admission to intensive care.

6. The method as claimed in claim 1, wherein the biological samples are blood samples.

7. The method as claimed in claim 1, wherein the dose of gelsolin is determined by a technique chosen from mass spectrometry and immunoassay.

8. The method as claimed in claim 1, wherein the patient is selected from multiple-trauma patients, what are referred to as major burns patients, patients suffering from pancreatitis or acute respiratory syndrome.

9. The method as claimed in claim 6, wherein the blood samples are whole blood, plasma, or serum.

10. A method comprising:
determining, via immunoassay or mass spectrometry, a first amount of gelsolin G1 in a biological sample from a patient admitted to intensive care having no clinical symptoms of a disseminated infection, the biological sample originating from a first sample taken at the time T1, carried out between the day of admission to intensive care and 48 hours afterward; and
determining, via immunoassay or mass spectrometry, a second amount of gelsolin G2 in a biological sample from the patient originating from a second sample taken at the time T2, carried out two to three days after the first sampling.

11. A method for predicting the risk of developing a disseminated infection in a patient admitted to intensive care having no clinical symptoms of such an infection, the method comprising:
determining a first amount of gelsolin G1 in a biological sample from the patient originating from a first sample taken at the time T1, carried out between the day of admission to intensive care and 48 hours afterward;
determining a second amount of gelsolin G2 in a biological sample from the patient originating from a second sample taken at the time T2, carried out two to three days after the first sampling;
calculating the variation between the amount of gelsolin G2 and the amount of gelsolin G1, giving a Δ value;
comparing the Δ value obtained in the preceding step to a threshold value S determined beforehand from two populations of patients admitted to intensive care, one not having developed a disseminated infection and the other having developed such an infection, wherein:
a Δ value lower than said threshold value S means that the patient admitted to intensive care is a patient at high risk of developing a disseminated infection, and
a Δ value greater than said threshold value S means that the patient admitted to intensive care is not a patient at high risk of developing a disseminated infection; and
treating the patient at high risk of developing a disseminated infection to reduce the risk of developing the disseminated infection.

12. The method according claim 11, wherein the treatment comprises prophylactic antibiotic treatment.

13. The method according claim 11, wherein the treatment comprises immunotherapy.

14. The method according claim 11, wherein the treatment comprises reducing points of entry of pathogens to the patient.

* * * * *